(12) United States Patent
Howard

(10) Patent No.: US 9,715,807 B2
(45) Date of Patent: Jul. 25, 2017

(54) WIRELESS DEVICE AND METHODS FOR USE IN DETERMINING CLASSROOM ATTENDANCE

(71) Applicant: THL Holding Company, LLC, Round Rock, TX (US)

(72) Inventor: John W. Howard, Cedar Park, TX (US)

(73) Assignee: THL HOLDING COMPANY, LLC, Round Rock, TX (US)

( * ) Notice: Subject to any disclaimer, the term of this patent is extended or adjusted under 35 U.S.C. 154(b) by 0 days.

(21) Appl. No.: 14/932,526

(22) Filed: Nov. 4, 2015

(65) Prior Publication Data

US 2016/0055732 A1    Feb. 25, 2016

Related U.S. Application Data

(63) Continuation-in-part of application No. 14/281,077, filed on May 19, 2014, now Pat. No. 9,295,024,
(Continued)

(51) Int. Cl.
*G08B 21/02* (2006.01)
*H04W 8/00* (2009.01)
(Continued)

(52) U.S. Cl.
CPC ..... *G08B 21/0272* (2013.01); *G06K 9/00288* (2013.01); *G08B 13/1427* (2013.01);
(Continued)

(58) Field of Classification Search
CPC ......... G06K 9/00288; G06K 19/07749; G08B 13/1427; G08B 21/0247; G08B 21/0269;
(Continued)

(56) References Cited

U.S. PATENT DOCUMENTS

| 5,956,696 A * | 9/1999 | Guryel ................. G06Q 10/087 705/28 |
| 2006/0035205 A1* | 2/2006 | Dobson ............... G07C 9/00111 434/350 |

(Continued)

*Primary Examiner* — Hung T Nguyen
(74) *Attorney, Agent, or Firm* — Garlick & Markison; Bruce E. Stuckman

(57) ABSTRACT

Various embodiments include, for example, a wireless device that includes a short-range wireless transceiver to communicate RF signals including a beacon signal to identify the wireless device and to facilitate the association of the wireless device with the plurality of mobile communication devices in proximity to the wireless device. Each corresponding one of the plurality of mobile communication devices includes a mobile communication device processor that executes a student application, downloaded from an app store associated with the operating system of the corresponding one of the plurality of mobile communication devices that facilitates location of the corresponding one of the plurality of mobile communication devices. Attendance data is stored indicating that a student associated each corresponding one of the plurality of mobile communication devices is in a classroom associated with the wireless device. Other embodiments are disclosed.

20 Claims, 25 Drawing Sheets

Related U.S. Application Data which is a continuation of application No. 14/044,202, filed on Oct. 2, 2013, now Pat. No. 8,768,381, which is a continuation of application No. 12/713,346, filed on Feb. 26, 2010, now Pat. No. 8,588,806.

(51) Int. Cl.

| | |
|---|---|
| *H04W 4/00* | (2009.01) |
| *H04W 4/02* | (2009.01) |
| *G06K 9/00* | (2006.01) |
| *G08B 13/14* | (2006.01) |
| *H04W 4/20* | (2009.01) |
| *G08B 25/01* | (2006.01) |
| *G08B 5/22* | (2006.01) |
| *H04W 84/18* | (2009.01) |

(52) U.S. Cl.
CPC ..... *G08B 21/0244* (2013.01); *G08B 21/0247* (2013.01); *G08B 21/0269* (2013.01); *G08B 21/0277* (2013.01); *H04W 4/008* (2013.01); *H04W 4/02* (2013.01); *H04W 4/021* (2013.01); *H04W 4/20* (2013.01); *H04W 8/005* (2013.01); *G08B 5/22* (2013.01); *G08B 25/016* (2013.01); *H04W 84/18* (2013.01)

(58) Field of Classification Search
CPC .......... G08B 21/0272; G06Q 10/0833; H04W 4/008; H04W 8/005; H04W 4/021
USPC ............ 340/539.11, 539.13, 539.19, 539.23; 705/28, 32; 709/203, 232; 382/118, 120
See application file for complete search history.

(56) References Cited

U.S. PATENT DOCUMENTS

| | | | |
|---|---|---|---|
| 2008/0040502 | A1* | 2/2008 | Holsberry .............. G06Q 50/20 709/232 |
| 2008/0272905 | A1* | 11/2008 | Higaki ................ G06Q 10/109 340/539.11 |

\* cited by examiner

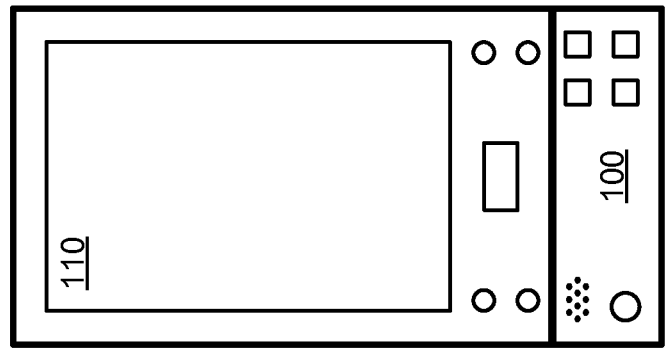
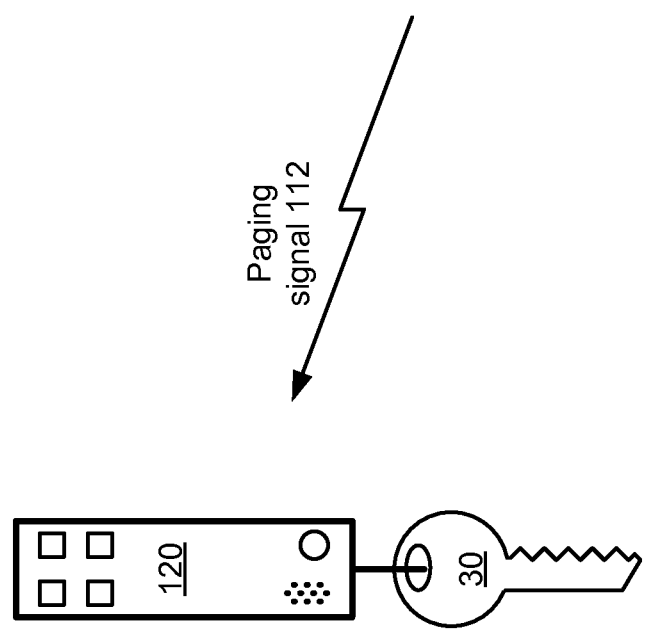
FIG. 4

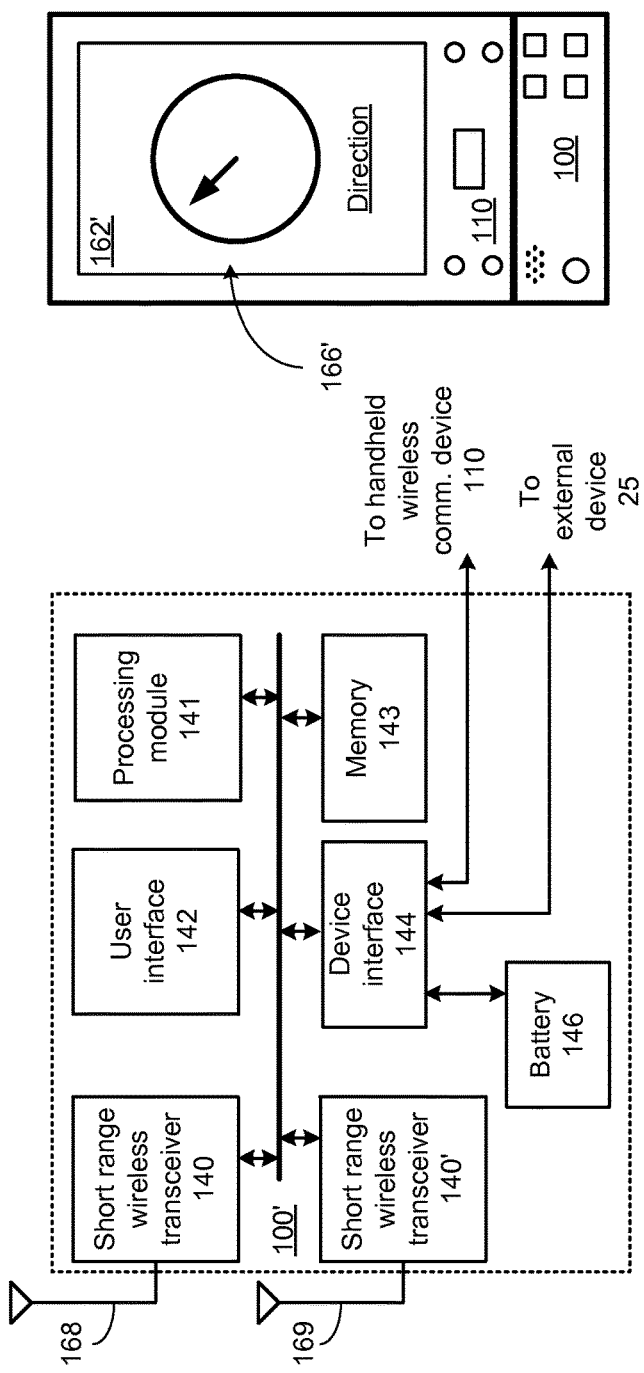
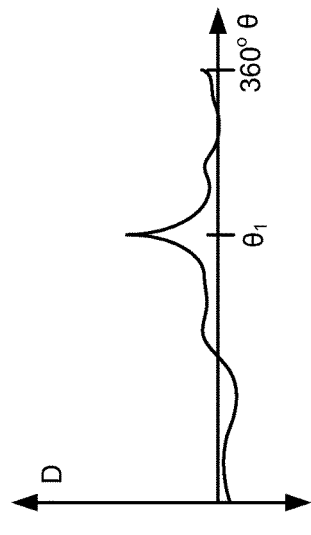
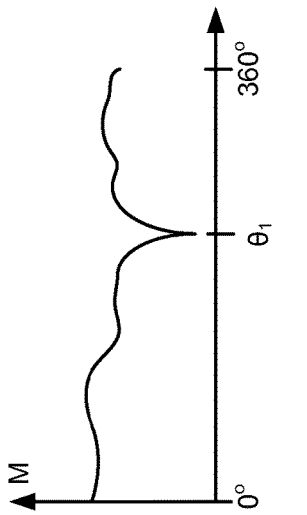
FIG. 15
FIG. 14
FIG. 13
FIG. 12

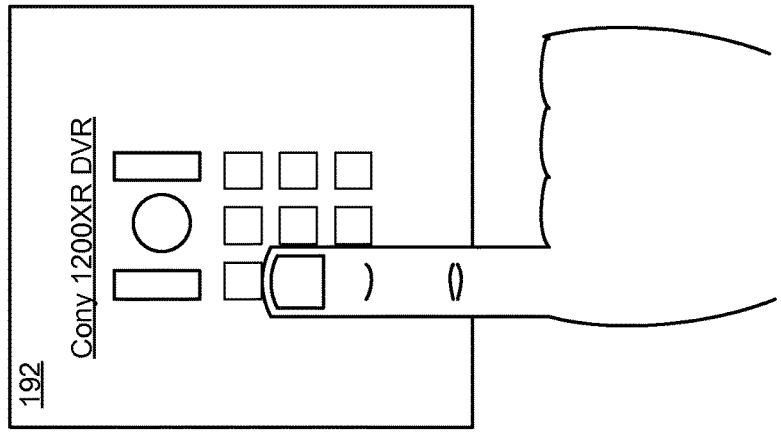
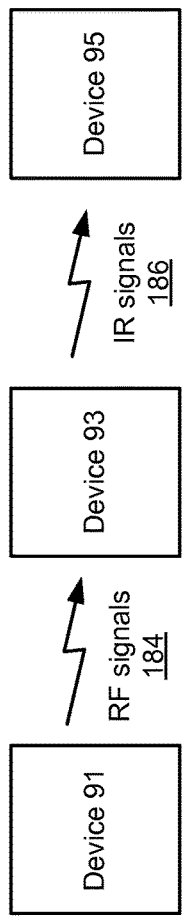
FIG. 21
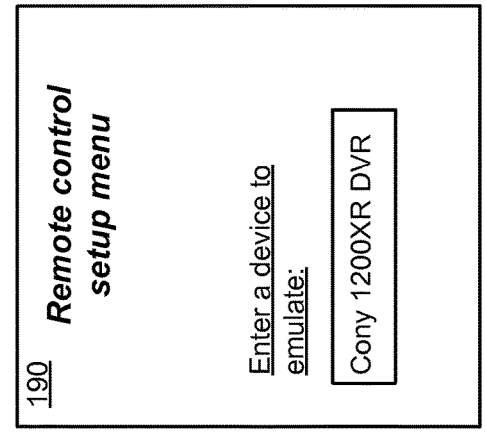
FIG. 22
FIG. 23

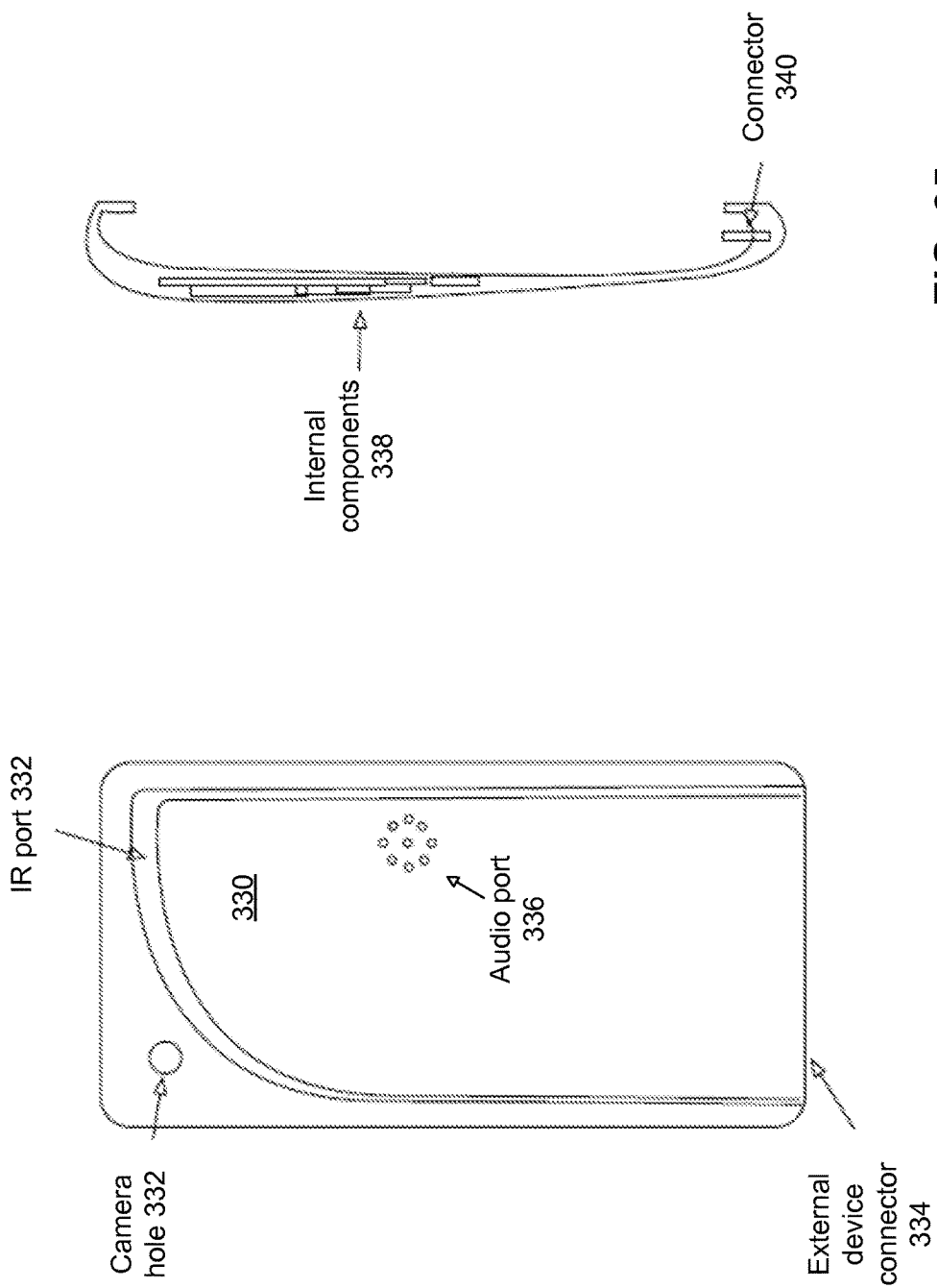

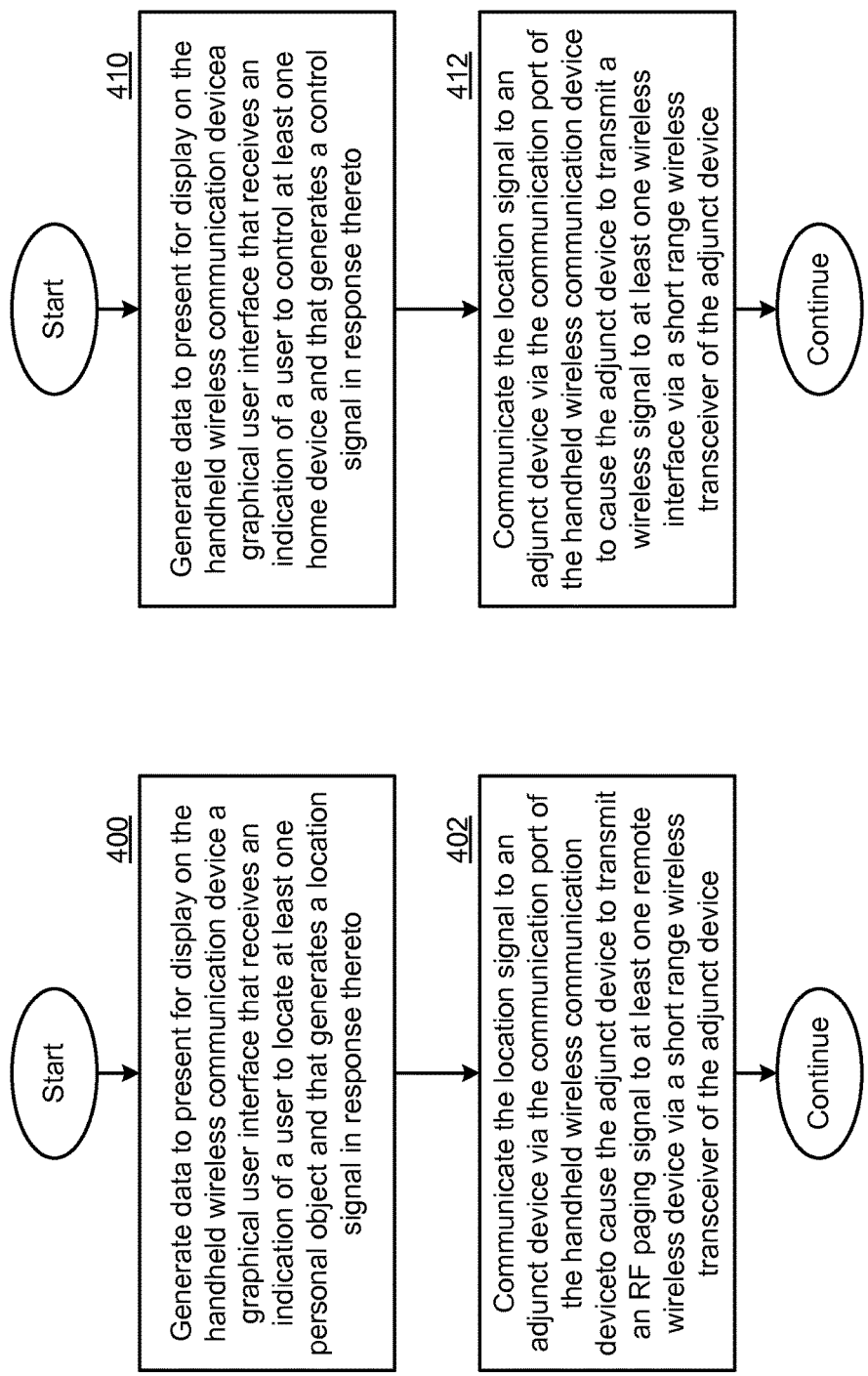

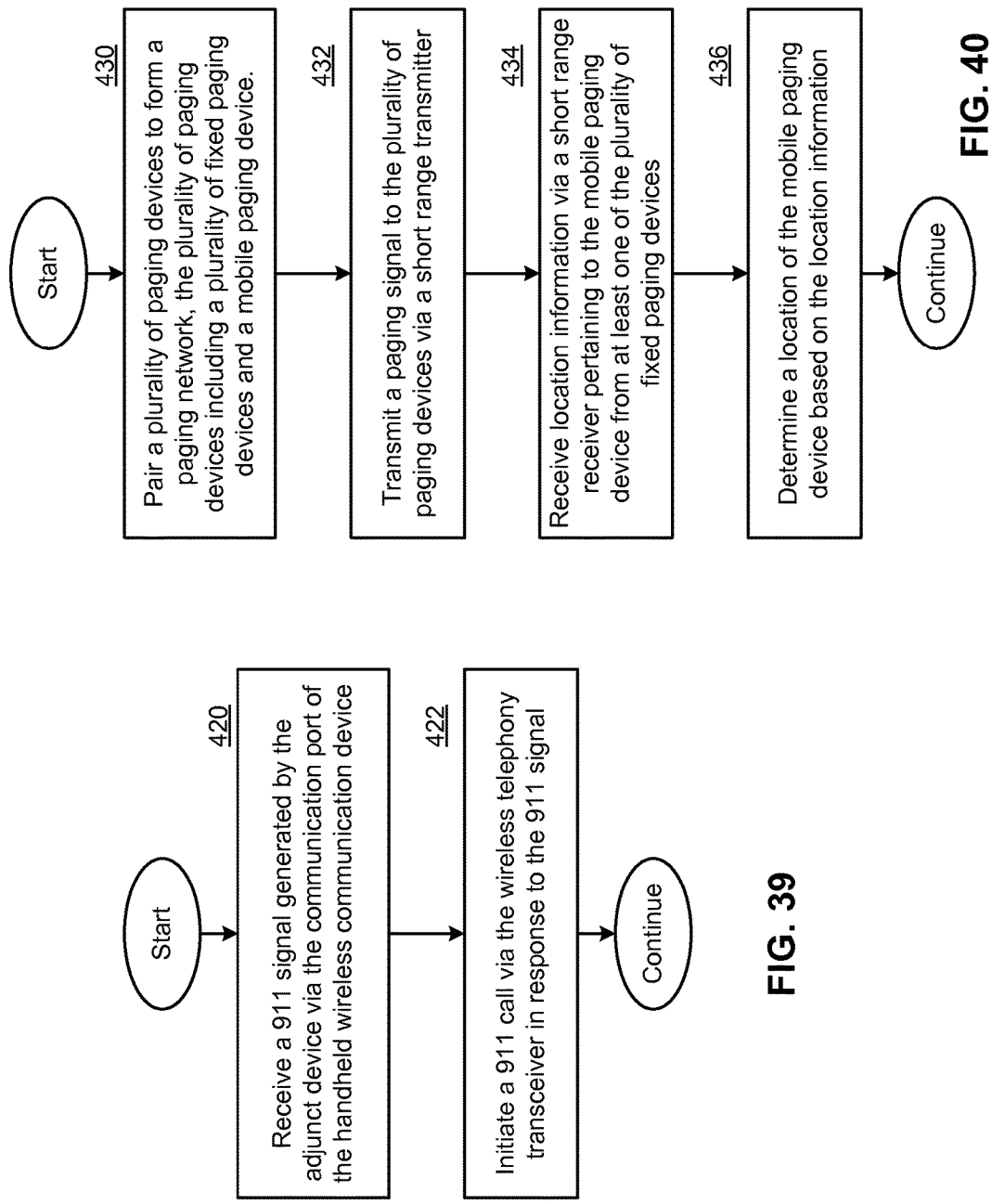

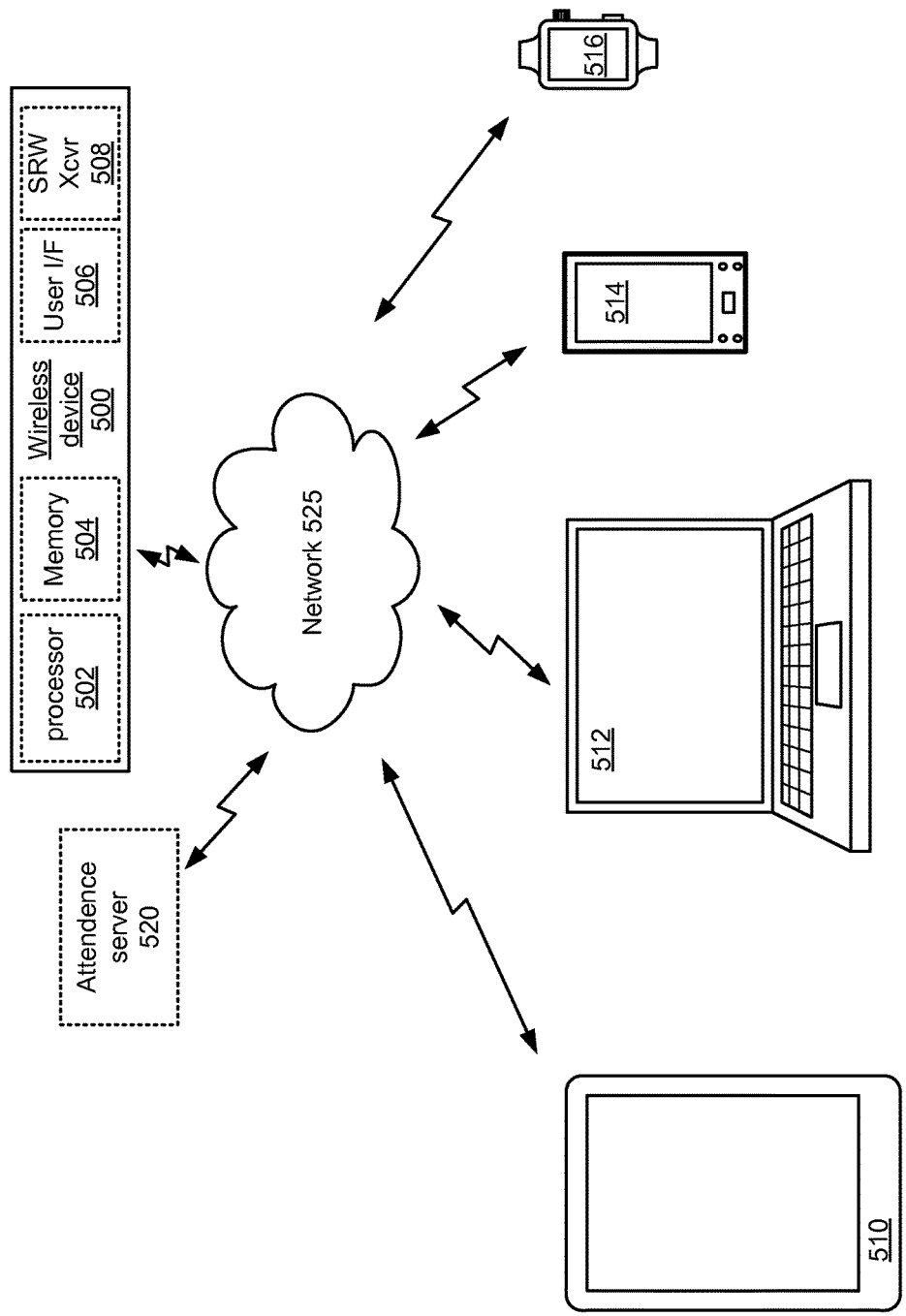

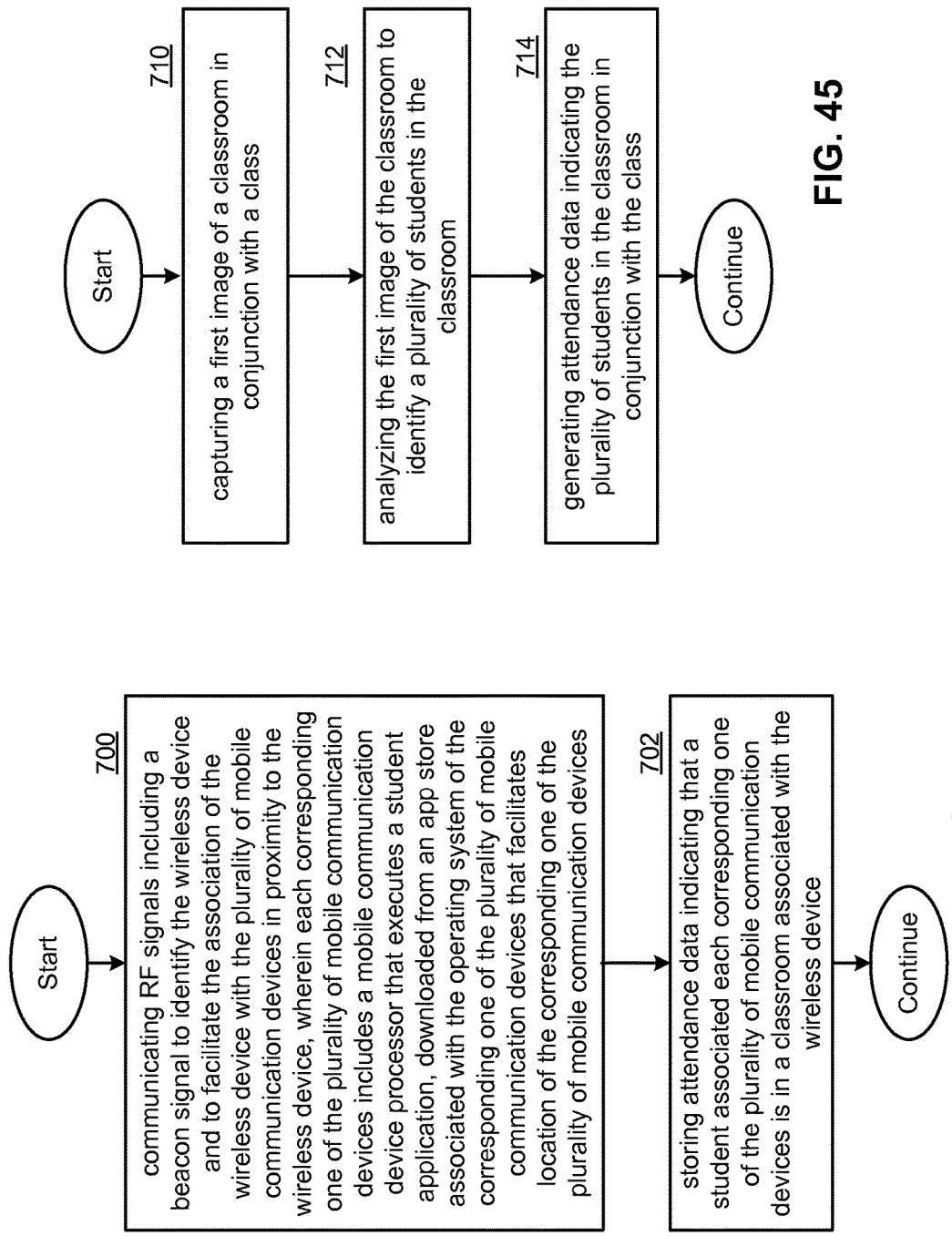

WIRELESS DEVICE AND METHODS FOR USE IN DETERMINING CLASSROOM ATTENDANCE

CROSS REFERENCE TO RELATED APPLICATIONS

The present U.S. Utility patent application also claims priority pursuant to 35 U.S.C. §120 as a continuation-in-part of U.S. Utility application No. 14/281,077, entitled "WIRELESS DEVICE AND METHODS FOR USE IN A PAGING NETWORK", filed May 19, 2014 U.S. Pat. No. 9,254,024, which is a continuation of U.S. Utility application No. 14/044,202, entitled "WIRELESS DEVICE AND METHODS FOR USE IN A PAGING NETWORK", filed Oct. 2, 2013, issued as U.S. Pat. No. 8,768,381 on Jul. 1, 2014, which is a continuation of U.S. Utility application Ser. No. 12/713,346, entitled "WIRELESS DEVICE AND METHODS FOR USE IN A PAGING NETWORK", filed Feb. 26, 2010, issued as U.S. Pat. No. 8,588,806 on Nov. 19, 2013, all of which are hereby incorporated herein by reference in their entirety and made part of the present U.S. Utility patent application for all purposes.

BACKGROUND OF THE DISCLOSURE

Technical Field of the Disclosure

The present disclosure relates to wireless communication devices.

Description of Related Art

As is known, wireless communication devices are commonly used to access long range communication networks as well as broadband data networks that provide text messaging, email services, Internet access and enhanced features such as streaming audio and video, television service, etc., in accordance with international wireless communications standards such as 2G, 2.5G, 3G and 4G. Examples of such networks include wireless telephone networks that operate cellular, personal communications service (PCS), general packet radio service (GPRS), global system for mobile communications (GSM), and integrated digital enhanced network (iDEN).

Many wireless telephones have operating systems that can run applications that perform additional features and functions. Apart from strictly wireless telephony and messaging, wireless telephones have become general platforms for a plethora of functions associated with, for example, navigational systems, social networking, electronic organizers, audio/video players, shopping tools, and electronic games. Users have the ability to choose a wireless telephone and associated applications that meet the particular needs of that user. Consequently, the wireless telephone has, in some ways, become an important device for many aspects of the user's life. Misplacing a user's wireless telephone can be an annoying experience. Further, while a wide range of wireless telephones and applications are available today, other functions and features are desirable, particularly for use in conjunction with other wireless devices.

The disadvantages of conventional approaches will be evident to one skilled in the art when presented the disclosure that follows.

BRIEF DESCRIPTION OF THE SEVERAL VIEWS OF THE DRAWINGS

FIG. 4 presents a pictorial representation of a location system for use with a handheld wireless communication device 110 in accordance with an embodiment of the present disclosure.

FIG. 12 presents a graphical representation of a signal magnitude in accordance with an embodiment of the present disclosure.

FIG. 13 presents a schematic block diagram of adjunct device 100 in accordance with an embodiment of the present disclosure.

FIG. 14 presents a graphical representation of a difference signal in accordance with an embodiment of the present disclosure.

FIG. 15 presents a pictorial representation of handheld wireless communication device 110 and adjunct device 100 in accordance with an embodiment of the present disclosure.

FIG. 21 presents a schematic block diagram of devices 91, 93 and 95 in accordance with an embodiment of the present disclosure.

FIG. 22 presents a pictorial representation of a screen display 190 in accordance with an embodiment of the present disclosure.

FIG. 23 presents a pictorial representation of a screen display 192 in accordance with an embodiment of the present disclosure.

FIG. 34 presents a pictorial representation of a back view of an adjunct device 330 in accordance with an embodiment of the present disclosure.

FIG. 35 presents a pictorial representation of a cutaway side view of an adjunct device 330 in accordance with an embodiment of the present disclosure.

FIG. 37 presents a flowchart representation of a method in accordance with an embodiment of the present disclosure.

FIG. 38 presents a flowchart representation of a method in accordance with an embodiment of the present disclosure.

FIG. 39 presents a flowchart representation of a method in accordance with an embodiment of the present disclosure.

FIG. 40 presents a flowchart representation of a method in accordance with an embodiment of the present disclosure.

FIG. 41 presents a block diagram representation of wireless device in accordance with an embodiment of the present disclosure.

FIG. 44 presents a flowchart representation of a method in accordance with an embodiment of the present disclosure.

FIG. 45 presents a flowchart representation of a method in accordance with an embodiment of the present disclosure.

DETAILED DESCRIPTION OF THE DISCLOSURE

Figure 1:
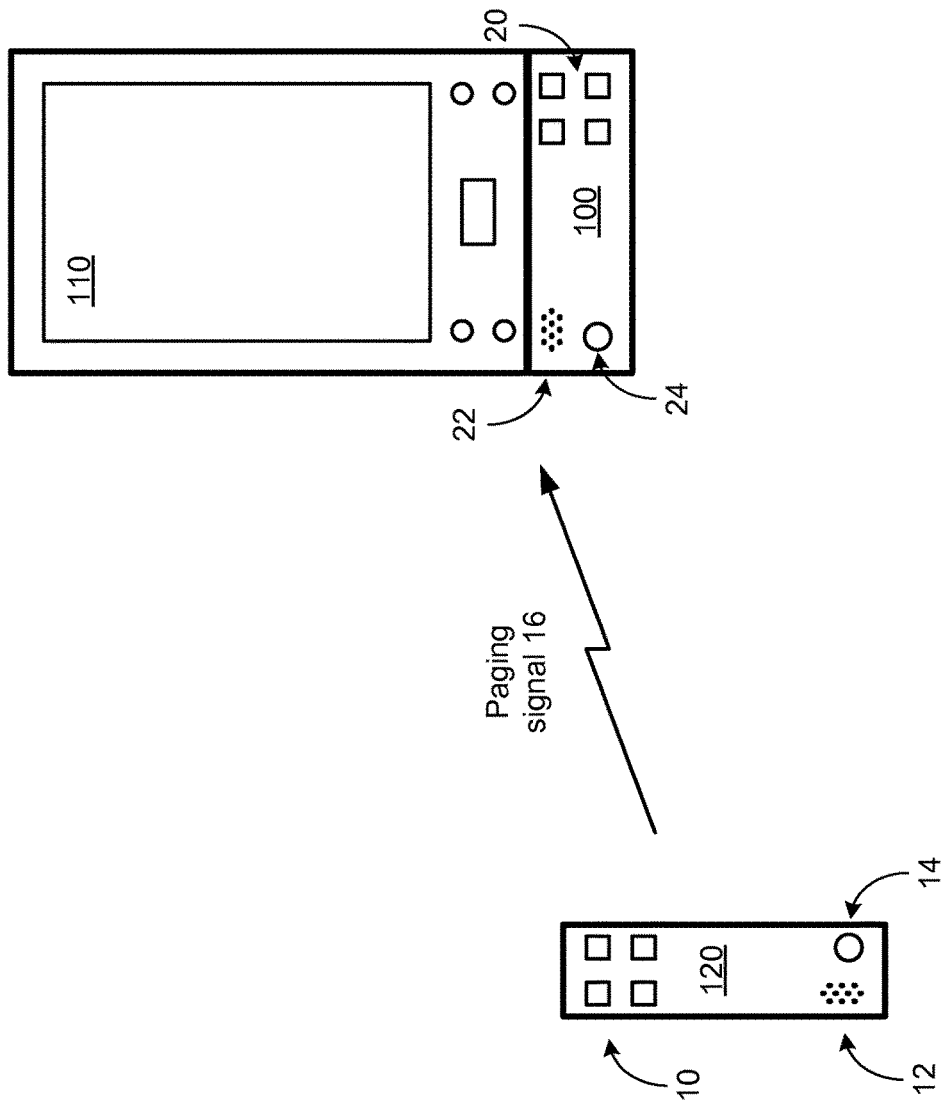
FIG. 1 presents a pictorial representation of a location system for use with a handheld wireless communication device 110 in accordance with an embodiment of the present disclosure.

FIG. 1 presents a pictorial representation of a location system for use with a handheld wireless communication device 110 in accordance with an embodiment of the present disclosure. In particular, a handheld wireless communication device 110, such as a smart phone, digital book, netbook, personal computer with wireless data communication or other wireless communication device that includes a wireless transceiver for communicating over a long range wireless network such as a cellular, PCS, CDMA, GPRS, GSM, iDEN or other wireless communications network and/or a short-range wireless network such as an IEEE 802.11 compatible network, a Wimax network, another wireless local area network connection or other communications link. Handheld wireless communication device 110 is capable of engaging in wireless communications such as sending and receiving telephone calls and/or wireless data in conjunction with text messages such as emails, short message service (SMS) messages, pages and other data messages that may include multimedia attachments, documents, audio files, video files, images and other graphics. Handheld wireless communication device 110 includes one or more processing devices for executing other applications and a user interface that includes, for example, buttons, a display screen such as a touch screen, a speaker, a microphone, a camera for capturing still and/or video images and/or other user interface devices.

Wireless device 120 is shown that includes a user interface that includes push buttons 10, a light emitter 14 such as a light emitting diode (LED) or other emitter, and sound emitter 12 such as a beeper, buzzer, speaker or other audio device. While particular user interface devices are shown, the wireless device can similarly include other devices such as a touch screen or other display screen, a thumb wheel, trackball, and/or other input or output devices. The user interface of the wireless device 120 generates a location request signal in response to an indication from a user by for instance, pushing one of the push buttons 10.

Wireless device 120 further includes a short-range wireless transmitter that transmits an RF paging signal, such as paging signal 16 in response to the location request signal. The short-range wireless transmitter can be part of a transceiver that operates in conjunction with a communication standard such as 802.11, Bluetooth, ZigBee, ultra-wideband, Wimax or other standard short or medium range communication protocol, or other protocol.

Adjunct device 100 includes a housing that is coupleable to the handheld wireless communication device 110 via a communication port of the handheld wireless communication device 110. The adjunct device 100 includes a short-range wireless receiver that receives the RF paging signal, such as paging signal 16. The short-range wireless receiver of adjunct 100 can also be part of a transceiver that operates in conjunction with a communication standard such as 802.11, Bluetooth, ZigBee, ultra-wideband, Wimax or other standard short or medium range communication protocol, or other protocol. In particular, the short-range wireless receiver of adjunct device 100 is configured to receive the paging signal 16 generated by wireless device 120.

Adjunct device includes its own user interface having push buttons 20, sound emitter 22 and light emitter 24 that emit audio and/or visual alert signals in response to the paging signal 16 to assist the user in locating the handheld wireless communication device. As with the user interface of wireless device 120, the user interface of adjunct device 100 can similarly include other devices such as a touch screen or other display screen, a thumb wheel, trackball, and/or other input or output devices.

In operation, a user can attach the adjunct device 100 to his or her handheld wireless communication device 110. If the handheld wireless communication device 110 is lost or mislaid, the user can locate the handheld wireless communication device by activating a paging button on the wireless device 120 that causes paging signal 16 to be broadcast. The adjunct device 100 responds to the paging signal 16 by flashing light emitter 24 and/or emitting a loud sound such as a beeping, buzzing or other alarm signal via sound emitter 22. The user can locate the handheld wireless communication device 110 by homing in on the visual and/or audio emissions.

The further operation of wireless device 120 and adjunct device 100, including several optional implementations, different features and functions spanning complementary embodiments are presented in conjunction with FIGS. 2-40 that follow.

Figure 3:
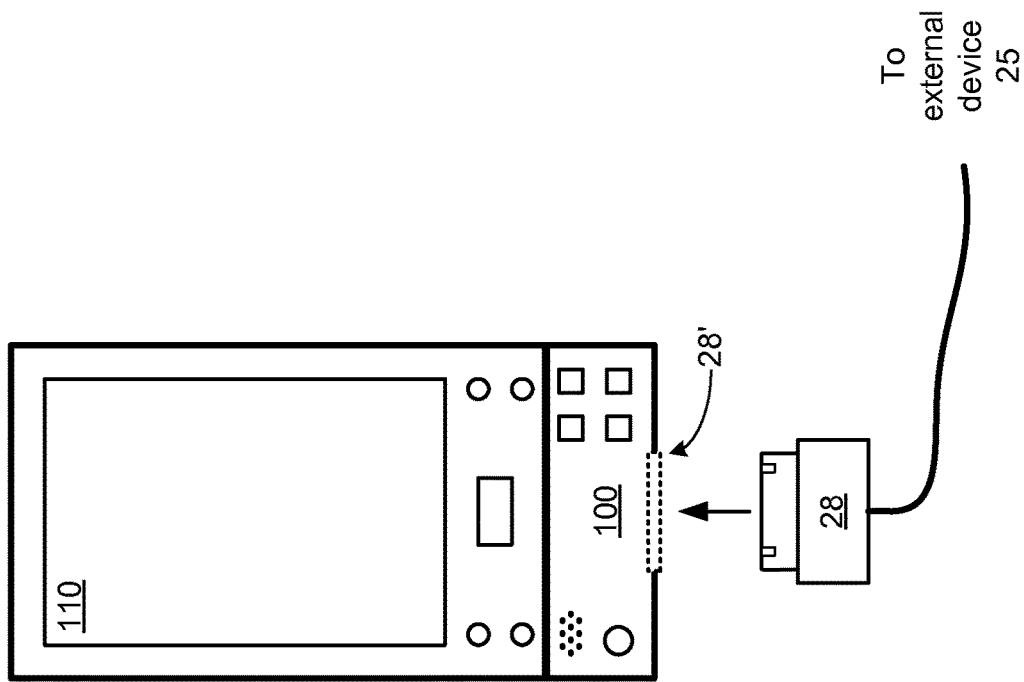
FIG. 3 presents a pictorial representation of handheld wireless communication device 110 and adjunct device 100 in accordance with an embodiment of the present disclosure.
Figure 2:
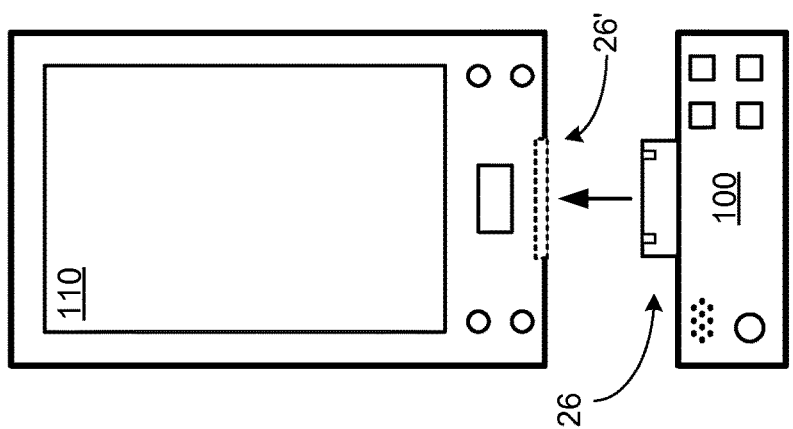
FIG. 2 presents a pictorial representation of handheld wireless communication device 110 and adjunct device 100 in accordance with an embodiment of the present disclosure.

FIGS. 2 and 3 present pictorial representations of handheld wireless communication device 110 and adjunct device 100 in accordance with an embodiment of the present disclosure. As shown in FIG. 2, adjunct device 100 and handheld wireless communication device 110 are decoupled. Handheld wireless communication device 110 includes a communication port 26' and adjunct device 100 includes a mating plug 26 for coupling the adjunct device 100 to the communication port 26' of handheld wireless communication device 110. In an embodiment of the present disclosure, the communication port 26' and plug 26 are configured in conjunction with a standard interface such as universal serial bus (USB), Firewire, or other standard interface, however, a device specific communication port such as an Apple iPod/iPhone port, a Motorola communication port or other communication port can likewise be employed. Further, while a physical connection is shown, a wireless connection, such as a Bluetooth link, 802.11 compatible link, an RFID connection or other wireless connection can be employed in accordance with alternative embodiments.

As shown in FIG. 3, adjunct device 100 is coupled to the handheld wireless communication device 110 by plug 26 being inserted in communication port 26'. Further, adjunct device 100 includes its own communication port 28' for coupling, via a mating plug 28, the adjunct device 100 to an external device 25, such as a computer or other host device, external charger or peripheral device. In an embodiment of the present disclosure, the communication port 28' and plug 28 are configured in conjunction with a standard interface such as universal serial bus (USB), Firewire, or other standard interface, however, a device specific communication port such as an Apple iPod/iPhone port, a Motorola communication port or other communication port can likewise be employed.

In an embodiment of the present disclosure, the adjunct device passes signaling between the external device 25 and the handheld wireless communication device 110 including, for instance, charging signals from the external connection and data communicated between the handheld wireless communication device 110 and the external device 25. In this fashion, the external device can communicate with and/or charge the handheld wireless communication device with the adjunct device 100 attached, via pass through of signals from plug 28 to communication port 26'. It should be noted however, that while communication ports 28' and 26' can share a common physical configuration, in another embodiment of the present disclosure, the communication ports 28' and 26' can be implemented via different physical configurations. For example, communication port 26' can be implemented via a device specific port that carries USB formatted data and charging signals and communication port 28' can be implemented via a standard USB port. Other examples are likewise possible.

In an embodiment of the present disclosure, when the adjunct device 100 is coupled to handheld wireless communication device 110, the adjunct device 100 initiates communication via the communication port 26' to determine if an application is loaded in the handheld wireless communication device 110—to support the interaction with the adjunct device 100. Examples of such applications include a location application or other application that operates in conjunction with the adjunct 100. If no such application is detected, the adjunct 100 can communicate via communication port 26' to initiate a download of such an application directly or to send the browser of the handheld wireless communication device 110 to a website store at a remote server or other location where supporting applications can be browsed, purchased or otherwise selected for download to the handheld wireless communication device 110.

In a further embodiment of the present disclosure, when a supporting application is loaded in handheld wireless communication device 110, the handheld wireless communication device 110 initiates communications via the communication port 26' to determine if an adjunct device 100 is coupled thereto or whether or not an adjunct device has never been coupled thereto. If no such adjunct device 100 is detected, the application can instruct the user to connect the adjunct device 100. Further, the application can, in response to user selection and/or an indication that an adjunct device has not been previously coupled to the handheld wireless communication device 110, automatically direct a browser of the handheld wireless communication device 110 to a website store at a remote server or other location where a supporting adjunct devices 100 can be selected and purchased, in order to facilitate the purchase of an adjunct device, via the handheld wireless communication device 110.

In a further embodiment, the application maintains a flag that indicates if an adjunct device 100 has previously been connected. In response to an indication that an adjunct device has not been previously coupled to the handheld wireless communication device 110, the application can automatically direct a browser of the handheld wireless communication device 110 to a website store at a remote server or other location where a supporting adjunct devices 100 can be selected and purchased, in order to facilitate the purchase of an adjunct device, via the handheld wireless communication device 110.

FIG. 4 presents a pictorial representation of a location system for use with a handheld wireless communication device 110 in accordance with an embodiment of the present disclosure. In particular, adjunct device 100 and wireless device 120 can operate in a reciprocal fashion to locate wireless device 120. In particular, wireless device 120 includes a housing that is attachable to or includes a ring, clip or other fastener that can be coupled to key 30 as shown or to another personal object such as a coat, a person, a pet or other thing. Further, wireless device 120 can be embodied as a card or other device that can be slipped into a wallet, an article of clothing, a bag or other thing to be located.

In any of these cases, the wireless device 120 includes its own short-range wireless receiver that receives a paging signal 112 transmitted by adjunct device 110. In response to the paging signal 112, a light or sound emitter of wireless device 120 emits a detectable alert signal that helps the user locate the personal object. In an embodiment of the present disclosure, the adjunct device 100 operates in a similar fashion to wireless device 120 to initiate the paging signal 112. In particular, the transmission of paging signal 112 can be initiated by pressing a button or otherwise interacting with the user interface of adjunct 100. In a further embodiment, handheld wireless communication device 100 includes an interactive application that generates application data that is passed to adjunct device 100 via the communication port of the handheld wireless communication device 100. Adjunct device 100 responds to such application data by initiating the transmission of the paging signal 112. In either case, a user of handheld wireless communication device 110 that wishes to locate his or her key 30, or other object coupled to wireless device 120, initiates the paging signal 112. The user can then locate the wireless device 120 and corresponding object by homing in on the visual and/or audio emissions of the wireless device 120.

Figure 5:
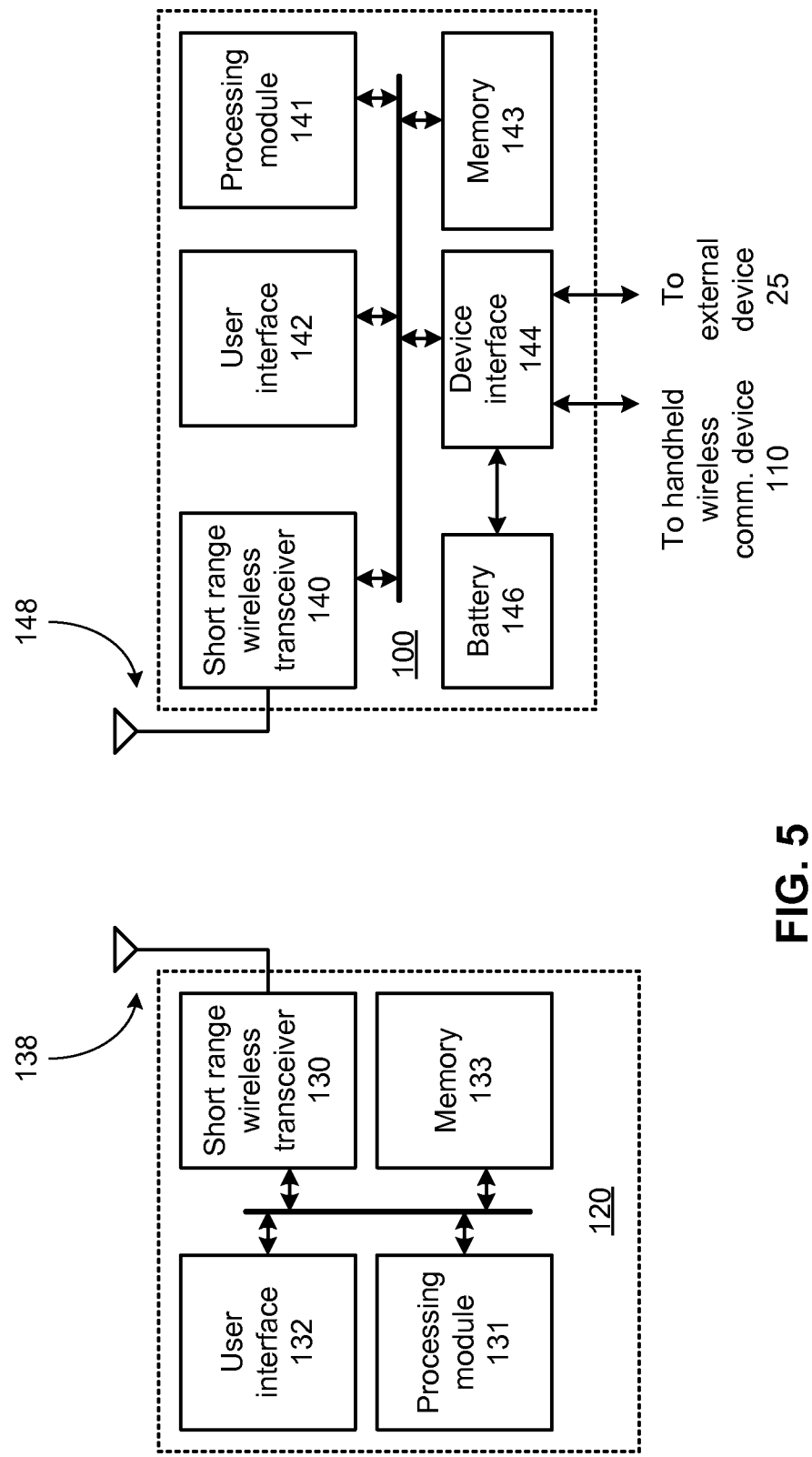
FIG. 5 presents a schematic block diagram of a wireless device 120 and adjunct device 100 in accordance with an embodiment of the present disclosure.

FIG. 5 presents a schematic block diagram of a wireless device 120 and adjunct device 100 in accordance with an embodiment of the present disclosure. In particular, wireless device 120 includes short-range wireless transceiver 130 coupled to antenna 138, processing module 131, user interface 132 and memory 133. While not expressly shown, wireless device 120 can include a replaceable battery for powering the components of wireless device 120. In the alternative, wireless device 120 can include a battery that is rechargeable via an external charging port, for powering the components of wireless device 120. Adjunct device 100 includes short-range wireless transceiver 140 coupled to antenna 148, processing module 141, user interface 142 and memory 143, device interface 144, and battery 146. The processing modules 131 and 141 control the operation of the wireless device 120 and adjunct device 100, respectively and provide further functionality described in conjunction with, and as a supplement to, the functions provided by the other components of wireless device 120 and adjunct device 100.

As discussed in conjunction with FIGS. 1-4, the short-range wireless transceivers 130 and 140 each can be implemented via a transceiver that operates in conjunction with a communication standard such as 802.11, Bluetooth, ZigBee, ultra-wideband, Wimax or other standard short or medium range communication protocol, or other protocol. User interfaces 132 and 142 each can contain one or more push buttons, a sound emitter, light emitter, a touch screen or other display screen, a thumb wheel, trackball, and/or other user interface devices.

The processing module 131 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 133. Note that when the processing module 131 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 133 stores, and the processing module 131 executes, operational instructions corresponding to at least some of the steps and/or functions illustrated herein.

The memory module 133 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of wireless device 120 are shown as being coupled by a particular bus structure, other architectures are likewise possible that include additional data busses and/or direct connectivity between components. Wireless device 120 can include additional components that are not expressly shown.

Likewise, the processing module 141 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 143. Note that when the processing module 141 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 143 stores, and the processing module 141 executes, operational instructions corresponding to at least some of the steps and/or functions illustrated herein.

The memory module 143 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of adjunct device 100 are shown as being coupled by a particular bus structure, other architectures are likewise possible that include additional data busses and/or direct connectivity between components. Adjunct device 100 can include additional components that are not expressly shown.

As shown, the adjunct device includes a battery 146 that is separate from the battery of the handheld wireless communication device 110 and can supply power to short-range wireless transceiver 140, processing module 141, user interface 142, memory 143, and device interface 144 in conjunction with a power management circuit, one or more voltage regulators or other supply circuitry. By being separately powered from the handheld wireless communication device 110, the adjunct 100 can operate even if the battery of the handheld wireless communication device is discharged. In this fashion, the user can still page the adjunct device 100 to locate the handheld wireless communication device 110 when the battery of the handheld wireless communication device is discharged.

Device interface 144 provides an interface between the adjunct device 100 and the handheld wireless communication device 110 and an external device 25, such as a computer or other host device, peripheral or charging unit. As previously discussed in conjunction with FIGS. 1-4, the housing of adjunct device 100 includes a plug, such as plug 26, or other coupling device for connection to the communication port 26' of the handheld wireless communication device 110. In addition, the housing of adjunct device 100 further includes its own communication port, such as communication port 28' or other coupler for connecting to an external device 25. Device interface 144 is coupled to the communication port 28' that operates as a charging port. When adjunct device 100 is connected to an external source of power, such as external device 25, device interface 144 couples a power signal from the external power source to charge the battery 146. In addition, the device interface 144 couples the power signal from the external power source to the communication port of the handheld wireless communication device 110 to charge the battery of the handheld wireless communication device. In this fashion, both the handheld wireless communication device 110 and the adjunct device 100 can be charged at the same time. Further, the handheld wireless communication device 110 can be charged while the devices are still coupled—without removing the adjunct device 100 from the handheld wireless communication device 110.

While the battery 146 is separate from the battery of the handheld wireless communication device 110, in an embodiment of the present disclosure, the device interface 144 is switchable between an auxiliary power mode and a battery isolation mode. In the battery isolation mode, the device interface 144 decouples the battery 146 from the battery of the handheld wireless communication device 110, for instance, to preserve the charge of battery 146 for operation even if the battery of the handheld wireless communication device 110 is completely or substantially discharged. In the auxiliary power mode, the device interface 144 couples the power from the battery 146 to the handheld wireless communication device 110 via the communication port to charge the battery of the handheld wireless communication device 110. In this fashion, the user of the handheld wireless communication device 110 at or near a discharged state of the handheld wireless communication device battery could opt to draw power from the battery 146. In an embodiment of the present disclosure, signaling from user interface 142 could be used to switch the device interface 144 between the battery isolation mode and the auxiliary power mode. Alternatively or in addition, signaling received from the handheld wireless communication device via the communication port, or remotely from wireless device 120, could be used to switch the device interface 144 between the battery isolation mode and the auxiliary power mode.

Device interface 144 includes one or more switches, transistors, relays, or other circuitry for selectively directing the flow of power between the external device 25, the battery 146, and the handheld wireless communication device 110 as previously described. In addition, the device interface 144 includes one or more signal paths, buffers or other circuitry to couple communications between the communication port of the adjunct device 110 and the communication port of the handheld wireless communication device 110 to pass through communications between the handheld wireless communication device 110 and an external device 25. In addition, the device interface 144 can send and receive data from the handheld wireless communication device 110 for communication between the adjunct device 100 and handheld wireless communication device 110.

Figure 6:
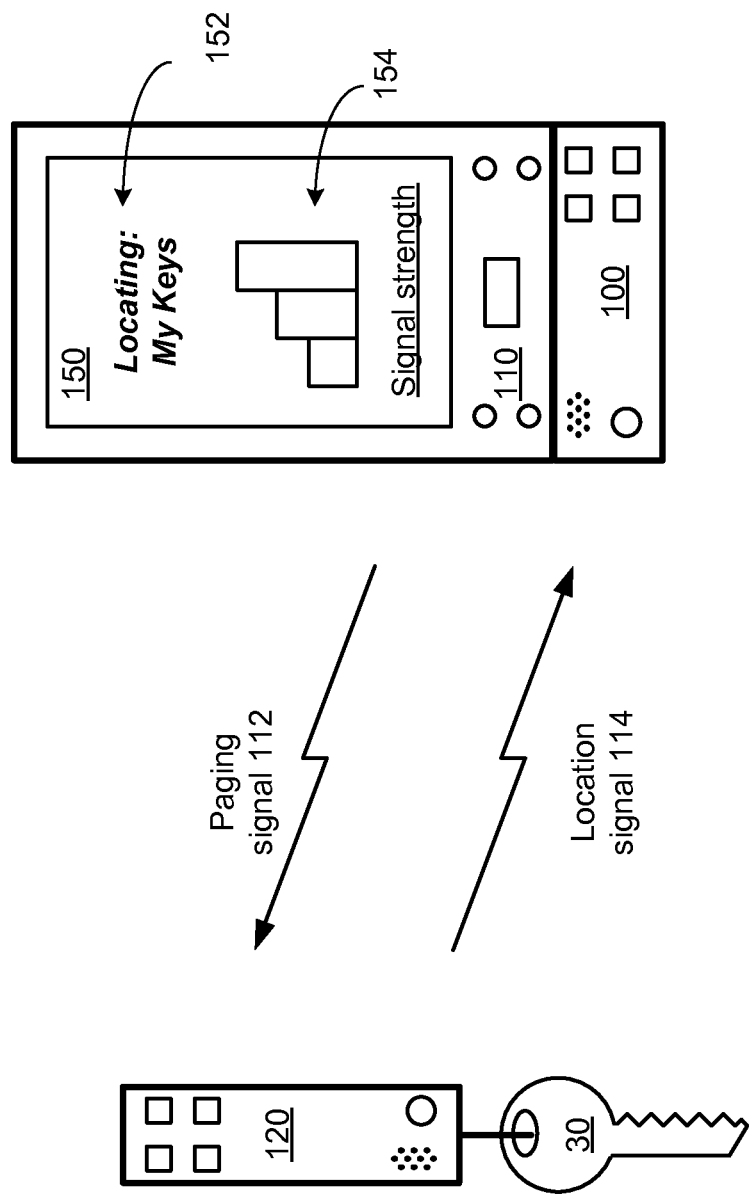
FIG. 6 presents a pictorial representation of a location system for use with a handheld wireless communication device 110 in accordance with an embodiment of the present disclosure.

FIG. 6 presents a pictorial representation of a location system for use with a handheld wireless communication device 110 in accordance with an embodiment of the present disclosure. In this embodiment, adjunct device 100 operates as previously described to transmit a paging signal 112. In this embodiment however, wireless device 120 transmits a location signal 114 via short-range wireless transceiver 130, such as a beacon signal or other location signal. Adjunct device 100 aids the user of handheld wireless communication device 110 in homing in on the location signal 114 based on the signal strength of the location signal 114 as received by short-range wireless transceiver 140.

In an embodiment of the present disclosure, the handheld wireless communication device 110 executes a location application that operates under user control to initiate the transmission of paging signal 112 to locate key or keys 30 or other object associated with wireless device 120. The signal strength of the location signal 114 from short-range wireless transceiver 140 is converted to signal strength data by processing module 141 and sent to handheld wireless communication device 110 via device interface 144 and the communication port of the handheld wireless communication device 110. The signal strength data is used by the location application to generate a graphical user interface including display screen 150. As shown, display screen 150 includes an indication 152 of the particular object being located and a visual signal strength indication 154. In this fashion, the user can move around with the handheld wireless communication device 110 and hunt for the key or keys 30, guided by changes in the visual signal strength indication 154. In particular, the user of handheld wireless communication device 110 can move about, seeking to maximize the visual signal strength indication 154 until the key or keys 30 are located.

While signal strength is described above as a measure of approximate distance to a remote device, the time of flight methodology described in conjunction with FIG. 37 or other distance approximations can likewise be employed.

Figure 7:
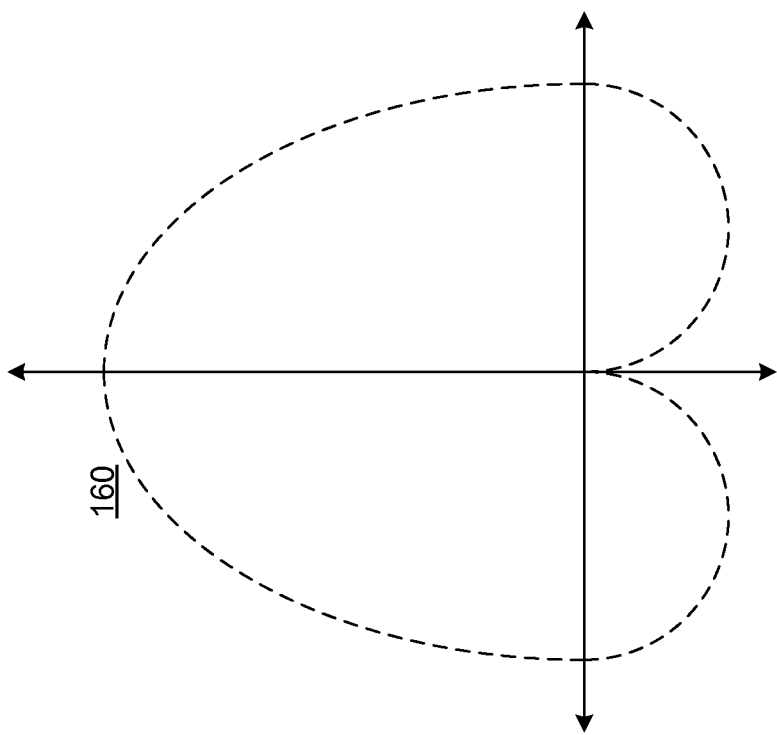
FIG. 7 presents a graphical representation of an antenna pattern in accordance with an embodiment of the present disclosure.

FIG. 7 presents a graphical representation of an antenna pattern in accordance with an embodiment of the present disclosure. A possible reception pattern of antenna 148 of adjunct device 100 is shown. The antenna pattern 160 is shown in two dimensions, corresponding to, for instance, the horizontal plane of the user. In particular, antenna 148 can include a pair of loop antennas, monopoles or dipoles or other antenna configurations that are aligned in position and phase to have a directional pattern that includes a single null. While a cardioid pattern is presented, other antenna patterns with a single null or with multiple nulls, such as multiple closely spaced nulls may also be employed.

As previously discussed, the short-range wireless transceiver 140 generates signal strength in response to the location signal 114 from wireless device 120. The signal strength is used to generate signal strength data that is communicated to the location application of handheld wireless communication device 110 via the communication port of the handheld wireless communication device. The use of a directional antenna in the implementation of antenna 148 can assist the location application in determining a direction to the wireless device 120. For example, the user can change the orientation of the handheld wireless communication device to determine the direction to the wireless device 120. The location application can detect when the orientation of the handheld wireless communication device corresponds to the direction of the wireless device, based on the signal strength data. When the null direction of the antenna 148 is pointing toward the wireless device 120, a null signal strength reading will occur. The location application can indicate a match to the user to inform him or her that the handheld wireless communication device 110 is pointed toward the wireless device 120.

In an alternative embodiment, the user is instructed to "turn around" to gather 360 degrees of directional data. The signal strength data can be analyzed in conjunction with one or more orientation sensors of the handheld wireless communication device 110, to determine a direction to the wireless device 120. In particular, the location application can determine the particular orientation of the device corresponding to the point where the null of antenna pattern 160 is aligned with the direction to the wireless device 120, and feedback that direction to the user via a directional indicator.

In an alternative embodiment, the antenna 148 includes a steerable pattern 160 that includes a steerable null. The location application of handheld wireless communication device 110 can, for example, instruct the user to stand still while the short-range wireless transceiver 140 completes a directional sweep. The location application sends application data to the adjunct device via device interface 144 that instructs the processing module 141 to command the programmable antenna to sweep the null direction by 360 degrees and to collect corresponding signal strength data. Analysis of the signal strength data by the location application can be used to determine the direction to the wireless device 120 based on the direction corresponding to the null. Feedback of that direction can be provided to the user via a directional indicator generated by the location application.

Further discussion of these features including several different embodiments and optional features are discussed in conjunction with FIGS. 8-15 that follow.

Figure 8:
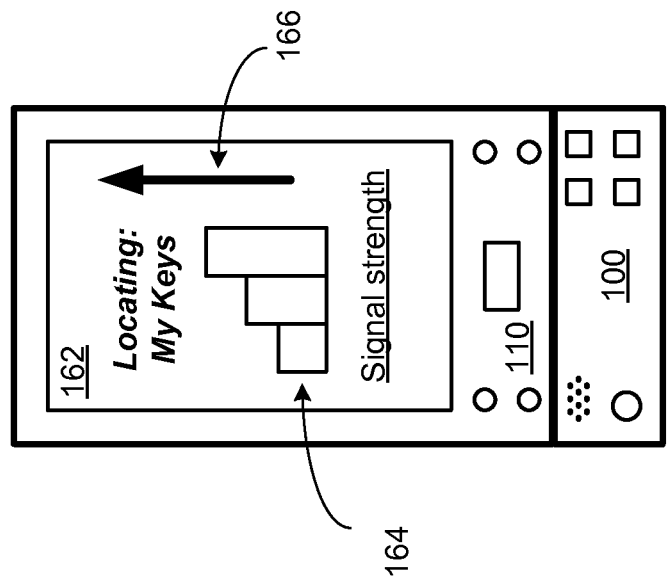
FIG. 8 presents a pictorial representation of handheld wireless communication device 110 and adjunct device 100 in accordance with an embodiment of the present disclosure.

FIG. 8 presents a pictorial representation of handheld wireless communication device 110 and adjunct device 100 in accordance with an embodiment of the present disclosure. In particular, a display screen 162 is shown that includes a signal strength indication 164 and an indication of direction 166 that can be used in conjunction with the location application examples discussed in association with FIG. 7. It should be noted that the location application of handheld wireless communication device 110 can operate to invert the signal strength data to generate the signal strength indication 164 so that when the null direction of the antenna pattern 160 is aligned with direction to wireless device 120, the low signal strength caused by the null is translated into a high signal strength indication, indicating to the user the device is pointed in the right direction.

In this particular embodiment, the indication of direction 166 is fixed, and is pointed in the null direction of the antenna 148. As the user changes the orientation of the handheld wireless communication device 110, the (inverted) signal strength indication 164 varies. When the inverted signal strength indication 164 peaks, this indicates that the null direction of the antenna 148 (and the indication of direction 166) is pointing toward the wireless device 120.

Figure 9:
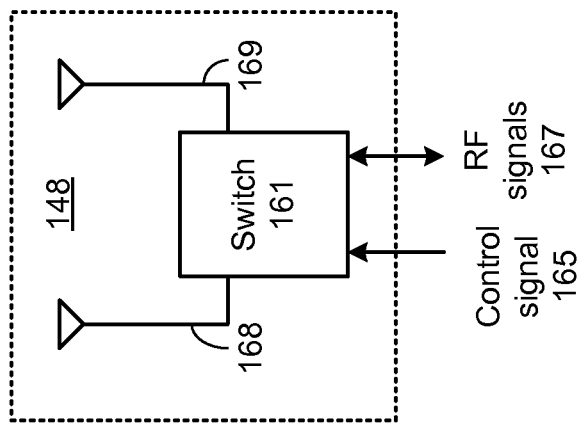
FIG. 9 presents a schematic block diagram of an antenna 148 in accordance with an embodiment of the present disclosure.

FIG. 9 presents a schematic block diagram of an antenna 148 in accordance with an embodiment of the present disclosure. In particular, antenna 148 includes two separate antennas 168 and 169 that are selectable by switch 161 in response to control signal 165. In an embodiment of the present disclosure, the antenna 168 is an omnidirectional or substantially omnidirectional antenna and antenna 169 has a radiation pattern that includes a null, as described in conjunction with FIGS. 7-8. RF signals 167 are sent or received by the particular antenna 168 or 169 that is selected. The control signal 165 can be generated by processing module 141 or application data from a location application of handheld wireless communication device 110.

In operation, control signal 165 is generated to select antenna 168 for standard operation. In this fashion, when the adjunct device 100 sends paging signals 112 or receives paging signal 16, signals can be received from all directions. When the adjunct device 100 is receiving location signals 114 from a remote wireless device 120, control signal 165 is generated to switch antenna 148 to antenna 169. In this fashion, the null pattern of antenna 169 can be used by the location application of handheld wireless communication device 110 to provide directional feedback to the user.

Figure 10:
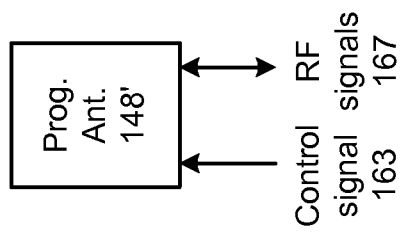
FIG. 10 presents a schematic block diagram of an antenna 148' in accordance with an embodiment of the present disclosure.

FIG. 10 presents a schematic block diagram of an antenna 148' in accordance with an embodiment of the present disclosure. In particular, antenna 148 is implemented via a programmable antenna 148' that has a controllable radiation pattern. In one mode of operation, the programmable antenna is controlled via control signal 163 to an omnidirectional or substantially omnidirectional antenna pattern. The control signal 163 can be generated by processing module 141 or application data from a location application of handheld wireless communication device 110. This mode of operation is selected when the adjunct device 100 sends paging signals 112 or receives paging signal 16. In this fashion, signals can be received from all directions.

When the adjunct device is receiving location signals 114 from a remote wireless device 120, control signal 163 is generated to switch antenna 148' to an antenna pattern, such as antenna pattern 160, and optionally to steer the null direction in conjunction with a directional sweep. In this mode of operation, the null pattern of antenna 148' can be used by the location application of handheld wireless communication device 110 to provide directional feedback to the user.

Figure 11:
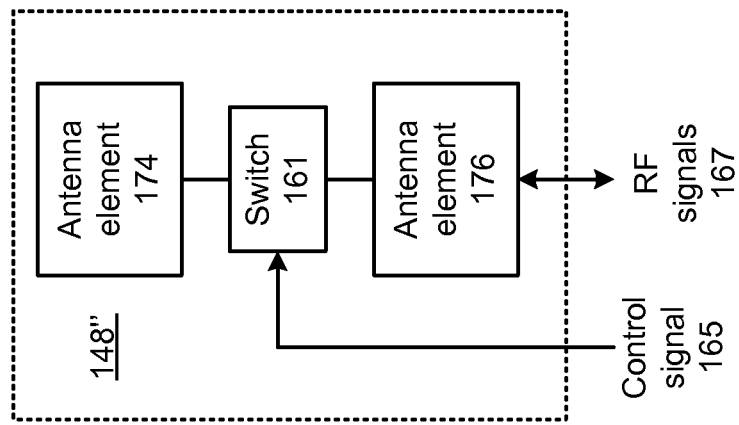
FIG. 11 presents a schematic block diagram of an antenna 148" in accordance with an embodiment of the present disclosure.

FIG. 11 presents a schematic block diagram of an antenna 148" in accordance with an embodiment of the present disclosure. In particular, antenna 148" is a programmable antenna that includes two separate antenna elements 176 and 174. The antenna 148" is configurable to a first configuration where switch 161 decouples antenna element 174 and only antenna element 176 is active. In a second configuration, switch 161 coupled antenna element 174 to antenna element 176 and both elements are active.

In an embodiment of the present disclosure, antenna elements 174 and 176 are separate loops, monopoles, dipoles or other antenna elements. The antenna formed by only antenna element 176 produces an omnidirectional or substantially omnidirectional antenna pattern. The antenna formed by the combined antenna with antenna elements 174 and 176 has a radiation pattern that includes a null. Antenna 148" can be operated in response to control signals 165 in a similar fashion to the antenna 148 of FIG. 9.

In operation, control signal 165 is generated to select the omnidirectional antenna configuration for standard operation. In this fashion, when the adjunct device 100 sends paging signals 112 or receives paging signal 16, signals can be received from all directions. When the adjunct device is receiving location signals 114 from a remote wireless device 120, control signal 165 is generated to switch antenna 148" to the second configuration. In this fashion, the null pattern of antenna 148" can be used by the location application of handheld wireless communication device 110 to provide directional feedback to the user.

FIG. 12 presents a graphical representation of a signal magnitude in accordance with an embodiment of the present disclosure. In particular, signal strength M represents signal strength data collected by short-range wireless transceiver 140 in response to location signal 114. As discussed in conjunction with FIGS. 7-11, an antenna having a null direction is used in this mode of operation of adjunct 100. Signal strength M is generated over a range of directions, such as over 360 degrees of rotation, either by manually steering the handheld wireless communication device 110 coupled to adjunct 100 in the case of a fixed antenna such as antenna 148 or 148", or by steering the beam of the antenna in an implementation of a programmable antenna, such as antenna 148'. In either case the direction to the wireless device 120 can be determined based on the direction $\theta_1$, where the antenna null is pointed at the wireless device 120. As shown, the null in the antenna pattern causes the signal strength data to dip in a recognizable way.

In an embodiment of the present disclosure, the direction $\theta_1$ is determined based on the direction of lowest signal magnitude M. However other methodologies including pattern recognition can be employed to analyze the characteristics of the signal strength data to recognize the null direction.

FIG. 13 presents a schematic block diagram representation of adjunct device 100' in accordance with an embodiment of the present disclosure. In particular, a further embodiment of adjunct device 100 is shown that includes many common elements of the embodiment of FIG. 5 that are referred to by common reference numerals. In addition, adjunct device 100' includes a second short-range wireless transceiver 140' and a second antenna 169.

In this embodiment, the antenna 168 is an omnidirectional or substantially omnidirectional antenna and antenna 169 has either a fixed or steerable radiation pattern that includes a null, as described in conjunction with antennas 148, 148', 148" or 169. In operation, when the adjunct device 100 sends paging signals 112 or receives paging signal 16, short-range wireless transceiver 140 is used and signals can be received from all directions. When the adjunct device is receiving location signals 114 from a remote wireless device 120, short-range wireless transceivers 140 and 140' are both engaged and generate separate signal strength data. A difference between the signal strength data corresponding to antennas 168 and 148' is used to determine the null direction. In this fashion, the difference between the signal strength data from the two signal paths can be used to distinguish between high loss conditions and a direction corresponding to a null.

FIG. 14 presents a graphical representation of a difference signal in accordance with an embodiment of the present disclosure. In particular, signal strength $D(\theta)$ represents the difference between the magnitude of the signal strength data collected by short-range wireless transceivers 140 and 140' in response to location signal 114. Representing the signal strength generated by the short-range wireless transceiver 140 as $SS_o(\theta)$, and the signal strength of the short-range wireless transceiver 140 as $SS_n(\theta)$, the difference $D(\theta)$, can be determined based on:

$$D(\theta)=|SS_o(\theta)|-|SS_n(\theta)|$$

As discussed in conjunction with FIGS. 7-13, signal strength difference $D(\theta)$ is generated over a range of directions, such as over 360 degrees of rotation, either by manually steering the handheld wireless communication device 110 coupled to adjunct 100 in the case of a fixed antenna, or by steering the null of the antenna in an implementation of a programmable antenna. In either case the direction to the wireless device 120 can be determined based on the direction $\theta_1$, where the antenna null is pointed at the wireless device 120. As shown, the null in the antenna pattern causes the difference in signal strength data to increase in a recognizable way.

In an embodiment of the present disclosure, the direction $\theta_1$ is determined based on the direction of highest signal magnitude $D(\theta)$. However other methodologies including pattern recognition can be employed to analyze the characteristics of the signal strength data to recognize the null direction.

FIG. 15 presents a pictorial representation of handheld wireless communication device 110 and adjunct device 100 in accordance with an embodiment of the present disclosure. In particular, a display screen 162' is shown that includes an indication of direction 166' that can be used in conjunction with the location application examples discussed in association with FIG. 7-14.

In this particular embodiment, the indication of direction 166' moves based on the repeated directional sweeps by a steerable antenna such as antenna 148'. Indication of direction 166' indicates, for instance, the direction $\theta_1$ as previously discussed. As the user changes the orientation of the handheld wireless communication device 110, indication of direction 166' varies based on the updated direction $\theta_1$. The indication of direction 166' can be used in this fashion to point the user in the direction of the wireless device 120.

It should be noted that while the embodiment of FIGS. 7-15 have discussed the use of one or more antennas with a null, an antenna with a single lobe pattern or a steerable lobe pattern could be employed in a similar fashion to detect signal peaks instead of signal nulls.

In yet another embodiment of the present disclosure, a single antenna 148 is employed that has an omnidirectional pattern at one frequency or range of frequencies, yet exhibits a null at another frequency or range of frequencies. In particular, a location signal, such as location signal 114, can be sent at frequency corresponding to the null pattern and received by short range wireless transceiver 140. Instead of switching antennas 168 and 169, or programming an antenna 148' to different patterns as described in conjunction with FIGS. 9-11, two different patterns can be implemented in the same antenna to support both omnidirectional and null modes of operation.

In a further embodiment of the present disclosure, a receive antenna is employed that includes a plurality of null directions at different compass points in two dimensions that are realized at different frequencies. For example, an antenna, such as antenna 148 can exhibit a plurality of null directions $\theta_i$, that each have a corresponding null frequency $f_i$. In particular, a location signal, such as location signal 114, can include a swept frequency chirp that begins at a low frequency and ends at a high frequency that includes each of the discrete frequencies $f_i$. The short range wireless transceiver 140 can determine the direction to the remote device by detecting the frequency $f_i$ where the null occurs, for example based on a lowest signal level, and correlating the null frequency, via a lookup table or other data structure, to the corresponding direction $\theta_i$.

While the foregoing description has focused on location in a two dimensional sense, three-dimensional location can be accomplished in a similar fashion. In particular, directional antennas can be employed in both the x-y and x-z or y-z planes to distinguish z-axis, as well as x and y axis, coordinates. It should be noted that multiple directional antennas can be employed that are arranged orthogonally or non-orthogonally as long as the null directions span either all or substantially all of three dimensional space or a portion of three dimensional space that is of interest. Furthermore, complex antenna designs with three-dimensional antenna patterns can likewise be employed in a similar fashion to determine directionality in three-dimensions. Three dimensional location can be useful, for example, in locating objects on different floors of a building or other structure such as a mine or a ship, determining of a person with a remote device has fallen overboard, as well as other three-dimensional applications. In addition, or alternative to providing three dimensional direction finding, multiple antennas can be employed in a diversity receiver that, for example includes two or more receivers. Such configurations can be employed to mitigate the effects of fading, multipath interference and other path losses to provide more stable reception of signals, and more stable measurement of signal strength, round trip signal delay, etc.

Figure 16:
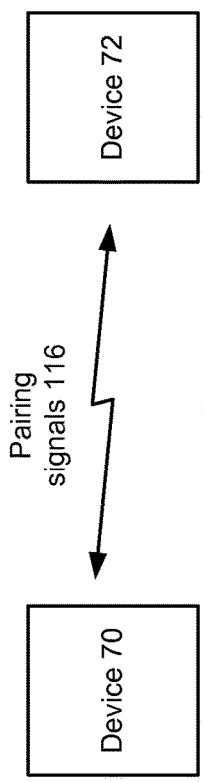
FIG. 16 presents a schematic block diagram of wireless devices 70 and 72 in accordance with an embodiment of the present disclosure.

FIG. 16 presents a schematic block diagram of wireless devices 70 and 72 in accordance with an embodiment of the present disclosure. In particular, the devices 70 and 72 can each be either a wireless device 120 or an adjunct device 100. The two devices can be sold as a set and are pre-paired to communicate with one another. In another embodiment of the present disclosure, the user can configure the devices 70 and 72 to be paired with one another.

In pairing, one or both devices 70 and 72 initiate the pairing procedure. For example, a user interface, such as user interface 132 or 142 generates a pairing signal in response to an indication from a user to pair the devices. A short-range wireless transceiver, such as short-range wireless transceiver 130 or 140, communicates RF signals, such as pairing signals 116 to pair the devices 70 and 72.

While two devices 70 and 72 are shown, three or more devices can be paired together in this fashion to form a paging network. In one mode of operation, paging signals, such as paging signals 16 or 112 sent by a single device are received by all other devices and cause each of the receiving devices to generate a detectable alert signal. In another mode of operation, paging signals 16 or 112 can be generated that are addressed to a particular unit, based on addresses or other identifiers received from or assigned to, each device during the pairing procedure. For example, each device 70, 72, . . . includes a unique device identifier that is shared with other devices during the pairing procedure. Paging signals, such as paging signals 16 or 112 can include the unique identifier to direct a paging signal to a particular device. In other words, when a device 70 or 72, receives a paging signal, it extracts the device identifier from the signal and compares it to its own device identifier stored in memory. If they match, the device emits a detectable alert. If the identifiers do not match, the page is presumed to be directed to another device and no alert is generated.

In an embodiment of the present disclosure, the paging signals 16 and/or 112 can further contain an identifier of the device that initiated the page. In this fashion, a device that receives a page and that is paired with multiple devices can determine which other device initiated the paging signal 16 or 112.

In an embodiment of the present disclosure, the paging signals 16 and/or 112 can also contain an paging data such as text, a text message, voice, graphics or other data that is conveyed from the device 70, 72 . . . that initiated the paging signal 16 or 112 and the device to the device that receives the page. This functionality creates the possibility of wireless device 120 and adjunct device 100 being used for applications, other than simply location of a lost object.

Figure 17:
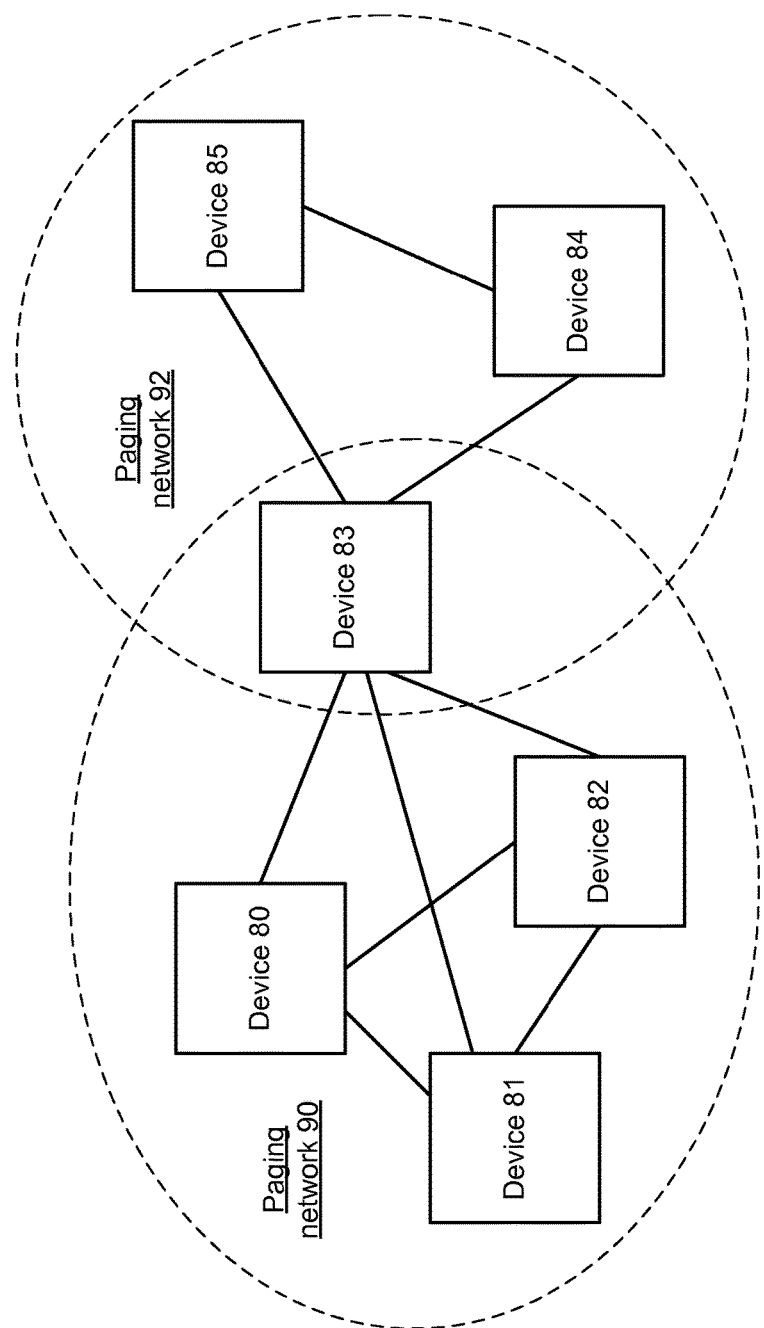
FIG. 17 presents a schematic block diagram of paging networks 90 and 92 in accordance with an embodiment of the present disclosure.

FIG. 17 presents a schematic block diagram of paging networks 90 and 92 in accordance with an embodiment of the present disclosure. In particular, paging network 90 includes devices 80-83 that have been paired together. In addition, paging network 92 includes devices 83-85 that have been paired together. The devices 80-85 can each be either a wireless device 120 or an adjunct device 100. As shown, device 83 has been paired with devices from both paging networks.

In a broadcast mode of operation, paging signals, such as paging signals 16 or 112 sent by a singe device, are received by all other devices in a network and cause each of the receiving devices to generate a detectable alert signal. In this fashion, devices 80-83 can each page all of the remaining devices in paging network 90. Devices 83-85 can each page all of the remaining devices in paging network 92. In an unicast mode of operation, paging signals 16 or 112 can be generated that are addressed to a particular unit, based on addresses or other identifiers received from or assigned to, each device during the pairing procedure. In this fashion, devices 80-83 can each page one of the remaining devices in paging network 90. Devices 83-85 can each page one of the remaining devices in paging network 92.

As discussed above, device 83 resides in both networks. Consequently, device 83 can be paged by a device from either network or can page devices from either network. However, in this configuration, device 80 from paging network 90 cannot page device 85 from paging network 92, and vice versa.

In an embodiment of the present disclosure, a device wishing to interact with another device repeatedly transmits a paging signal 16 or 112 for an interval of time greater than a listening device's wake-up-and-listen period. Say for example, a device wakes up every two seconds to "listen," the issuing device can transmit a paging signal 16 or 112 for three seconds. This strategy has obvious power consumption advantages.

While a paging application is discussed above, other applications, such as device tracking, can be enabled by the formation of paging networks 90 and 92 described above. Tracking can be implemented slightly differently. On wake-up, say every two seconds, a device transmits "tracking" information one time, then goes into listen mode to see if a paging signal 16 or 112 has been issued. The additional power consumption for the short transmit is nominal, as most of the power is consumed in the wake-up cycle itself. A device that "cares" to listen for location information can be placed into a state of listening for an extended time, say 3 seconds in our example, but it might do this only every 30 seconds, so this power hungry operation is not repeated very often. This tracking mode of operation allows a listening device to transmit useful information to any device that might care to take the time to listen periodically or on demand. In accordance with this example, a particular device 83 can be configured to track all other devices in the networks 90 and/or 92 in near real-time. The device 83 simply listens at appropriate intervals, as commanded, until all the desired information is collected from devices that are present in networks 90 and/or 92 without having to issue a paging signal 16 or 112, thus conserving battery power for both listener and talker.

In one application, the generation of location signals between devices can be used to determine if two devices are in proximity to one another. For example, devices 80-85 are associated with different people, objects, etc., and the location signals received by device 83 from devices 80-82 or 84-85, indicates which of these devices are present.

In this fashion, device 83 can determine which people or objects are in its proximity, or not in its proximity. For example, if device 83 is an adjunct associated with mom's wireless phone, device 80 is attached to the car keys and device 81 is an adjunct associated with her son's telephone, a mom can determine the proximity of her son and her keys. In response to location signals received by the adjunct device 83, the mom can determine whether or not her son and/or the car keys are in her proximity. A proximity application executed by her wireless phone can keep track of which of the devices 80-82 or 84-85 are in range and which are not, present alerts such as audible or visual alerts when a device comes in range or goes out of range, etc. In addition, the use of directional and/or distance information can augment the application to determine a nearest neighboring device or devices, plot estimated positions on a map, etc.

In addition to the applications listed above, other applications are possible including geo-caching and other social networking or gaming applications enabled by one or more devices that have been previously paired are auto-detected to determine the proximity of these devices and or the objects or persons associated therewith.

Figure 18:
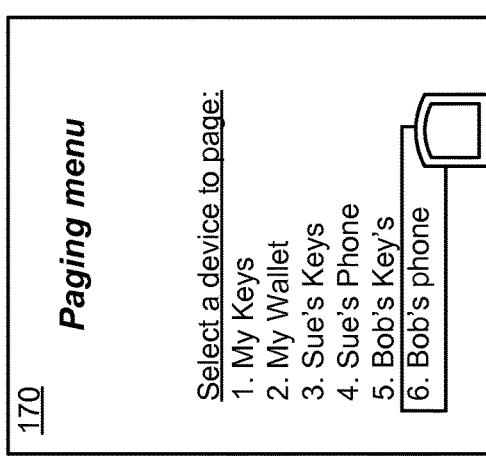
FIG. 18 presents a pictorial representation of a screen display 170 in accordance with an embodiment of the present disclosure.

FIG. 18 presents a pictorial representation of a screen display 170 in accordance with an embodiment of the present disclosure. In particular, a screen display 170 is shown for display via a graphical user interface generated by a location application of handheld wireless communication device 110. As shown, the graphical user interface includes a menu that indicates the plurality of personal objects, that each correspond to one of a plurality of remote device such as devices 70 or 72, or devices 80-85.

In an embodiment of the present disclosure, the pairing procedure described in conjunction with FIGS. 16-17 generates a list that identifies the plurality of remote devices and the plurality of personal objects. In particular, as a device is paired with the adjunct device 100, the location application of handheld wireless communication device queries the user to enter a name of an object or other identifier associated with the particular remote device being paired with the adjunct device 100. The names so entered are stored in the list in association with the device identifiers or other address information for the corresponding paired device that is either generated or received during the pairing process.

As shown, the paging menu is generated based on the list of objects—in this case, the objects identified 1-6. The user initiates a page to locate one of the objects via its wireless device 120 or adjunct device 100, by selecting the particular object from the menu.

Figure 19:
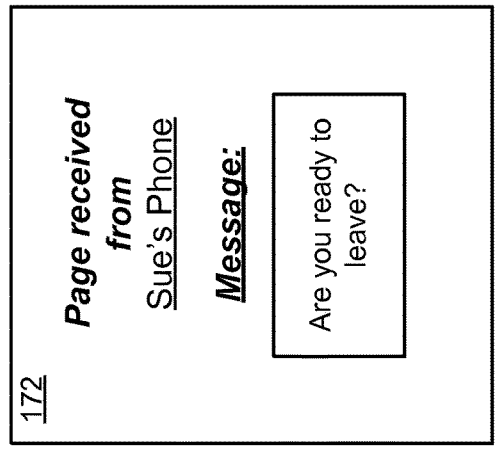
FIG. 19 presents a pictorial representation of a screen display 172 in accordance with an embodiment of the present disclosure.

FIG. 19 presents a pictorial representation of a screen display 172 in accordance with an embodiment of the present disclosure. In particular, a screen display 172 is shown for display via a graphical user interface generated by an application of handheld wireless communication device 110, such as a general paging application. As shown, the graphical user interface includes paging data received via paging signal 16 that indicates both the source of the page "Sue's Phone" and a text message, in this case, "Are you ready to leave?".

In operation, the text message is generated by a similar paging application of Sue's Phone that is coupled to its own adjunct device 100. The text message is included in the paging data and paging signals 112 sent via the adjunct device 100 of Sue's Phone. The paging data is received and decoded by the short-range wireless transceiver 140 of adjunct device 100—associated with the handheld wireless communication device 110 that generates screen display 172. The processing module 141 passes the paging data via the device interface 144 and communication port 26' of handheld wireless communication device 110 to the paging application. In addition to generating the detectable alert signal via the user interface 142 of adjunct device, the screen display 172 is generated by the paging application of handheld wireless communication device. As shown, this feature provides greater functionality in support of more advanced and complex applications.

Figure 20:
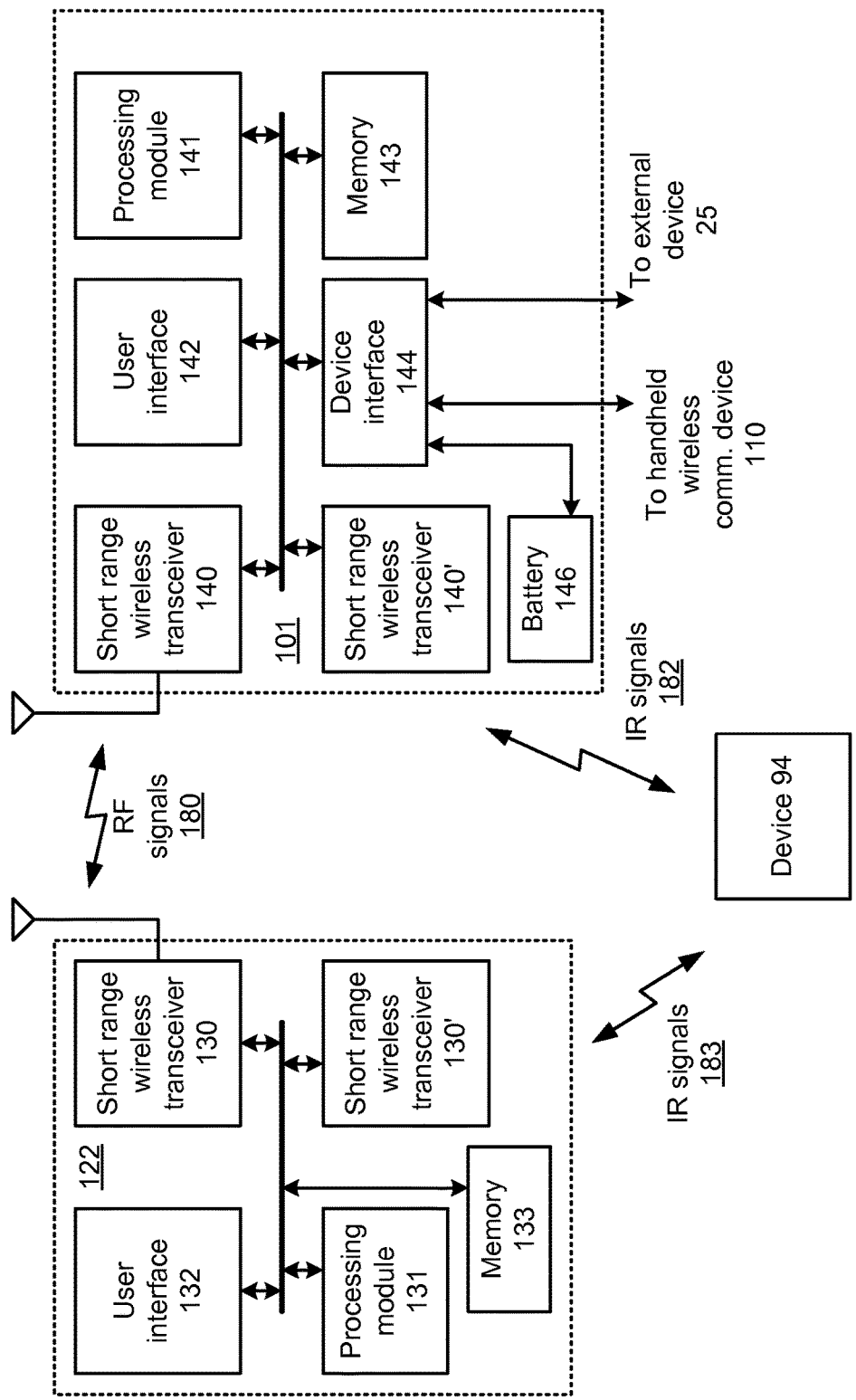
FIG. 20 presents a schematic block diagram of a wireless device 122 and adjunct device 101 in accordance with an embodiment of the present disclosure.

FIG. 20 presents a schematic block diagram of a wireless device 122 and adjunct device 101 in accordance with an embodiment of the present disclosure. In particular, wireless device 122 and adjunct device 101 include each of the components of wireless device 120 and adjunct device 100 previously described. In addition, the wireless device 122 and adjunct device 101 include short-range wireless transceivers 130' and 140' that each include infrared (IR) transmitters for sending IR signals, such as IR signals 182 and 183 to a remote device, such as device 94. Device 94 can be an automobile, alarm system, audio component, video component, game or other home media device or other device that is controlled in response to IR signals from an IR remote controller.

In an embodiment of the present disclosure, the adjunct device 100 is coupled to a handheld wireless communication device 110 that executes a remote control application that operates in a similar fashion to a universal remote control device for controlling the operation of a device 94 that operates based on IR remote control signals. In operation, the device interface 144 receives application data from the remote control application of the handheld wireless communication device 110 via the communication port of the handheld wireless communication device 110. The application data includes remote control data for controlling the operation of device 94. While a single device 94 is shown, the handheld wireless communication device 110 and adjunct device 101 can control a plurality of such devices in a similar fashion.

In an embodiment of the present disclosure, the short-range wireless transceiver 140' generates IR signals 182 based on the remote control data to directly control the operation of device 94. In a further embodiment, adjunct device 101 is paired with wireless device 122 to operate as an IR relay device. In this embodiment, the remote control data is transmitted via short-range wireless transceiver 140 via RF signals 180. Short-range wireless transceiver 130 receives and decodes the remote control data and retransmits the remote control data as IR signals 183 via short-range wireless transceiver 130'. In this further embodiment, the wireless device 122 can be located in close proximity and within line of sight with the device 94. The adjunct device 101 and handheld wireless communication device 110 can control the operation of device 94 from a different room or otherwise, while wireless device 122 is in range of RF signals 180.

While the foregoing description has focused on IR devices, in a similar fashion, devices 101, 122 and/or device 92 can include a short range wireless transceiver 130' or 140', such as a Bluetooth transceiver, 802.11 transceiver or other wireless transceiver that operates via RF signals. In one application, devices 101, 122 and/or device 92 can control a compatible remote device, such as device 94. In addition, the RF implementation of short-range wireless transceiver 130' or 140' can be used for other uses. In an embodiment of the present disclosure, paging signals or other messages can be transmitted to a home computer via a Bluetooth or 802.11 connection and relayed indirectly to the handheld wireless communication device 110 via the internet, wireless local area network and/or the long range wireless transceiver of the handheld wireless communication device 110.

FIG. 21 presents a schematic block diagram of devices 91, 93 and 95 in accordance with an embodiment of the present disclosure. In an embodiment of the present disclosure device 91 is implemented via adjunct device 101 and handheld wireless communication device 110, and device 93 is implemented via either wireless device 122 or adjunct device 101 and handheld wireless communication device 110 operating in a similar fashion to wireless device 122.

In a similar fashion to the system of FIG. 20, device 91 is paired with wireless device 93 to operate as an IR relay device. Remote control data is transmitted via RF signals 180. Device 93 receives the RF signals 184 and decodes the remote control data and retransmits the remote control data as IR signals 186 to control device 95.

FIG. 22 presents a pictorial representation of a screen display 190 in accordance with an embodiment of the present disclosure. In particular, a screen display 190 is shown that is generated by a remote control application for display on handheld wireless communication device 110. As shown, the user interacts with the remote control setup menu to enter one or more devices to be emulated. In the example shown, a hypothetical "Cony 1200XR DVR" device is selected. In response to the selection, the remote control application retrieves a remote control data configuration for this device from memory, such as the memory 143 of adjunct device 100 or the memory of the handheld wireless communication device so that remote control data transmitted as either RF signals 180 or IR signals 182 are properly formatted for control of the selected device. In an embodiment of the present disclosure, instead of storing remote control configuration data locally, the application contacts a remote server via the internet to retrieve the remote control configuration data. In this fashion, the long range transceiver or other wireless transceiver of handheld wireless communication device 110 can be used to gather remote control configuration data from an up to date list of current and legacy devices.

In a further mode of operation, remote graphics data corresponding to the look of the native remote control device for the selected "Cony 1200XR DVR" is also retrieved from memory, such as the memory 143 of adjunct device 100, the memory of the handheld wireless communication device, or from a remote server as described above. This remote graphics data can be used by the remote control application for emulating the look of the native remote control device for the selected "Cony 1200XR DVR", as will be shown further in conjunction with FIG. 23.

While not shown, the set-up menu may further prompt the user to establish one or more tasks to be performed by one or more devices to be controlled. In response, to these selections and the remote control configuration data retrieved for each device, the application can automatically establish a macro program to implement each task. In an example involving the control of a home media center, tasks might include: playing a DVD, watching TV, playing a CD, listening to the radio, playing a stored audio file or stored video file, accessing the internet to listen to streaming audio, accessing the internet to watch a streaming video, etc. For each selected task, the application configures the specific remote control operations required to control the devices of the home media center to states that correspond to the particular task.

In addition to task selection, the set-up menu may further prompt the user to establish one or more groups of devices to be controlled, and set up tasks associated with each group. For example, one group of devices might include the home media center in the living room, a second group of device might include the stereo in the bedroom, a third group of devices might include the lights in the dining room, etc.

FIG. 23 presents a pictorial representation of a screen display 192 in accordance with an embodiment of the present disclosure. In particular, a screen display 192 is shown that is generated by a remote control application for display on handheld wireless communication device 110. As shown, the display of handheld wireless communication device 110 creates a virtual remote control that emulates the look of the native remote control device for the device selected to be controlled—in this case, the "Cony 1200XR DVR". In operation, the user interacts with the virtual remote control to generate remote control data for controlling the selected device, either directly from adjunct device 100 or via an IR relay device such as wireless device 122.

In an alternative embodiment involving one or more tasks established as described in conjunction with FIG. 22, the screen display be "task oriented" instead of device oriented as shown in FIG. 23. For each selected task, the remote control application configures the screen display of the handheld wireless communication device 110 to implement a menu of the particular remote control commands associated with that particular task.

For instance, the user can be presented with a menu of groups that have been configured. Once a group has been selected, a menu of tasks associated with that group is presented. Once a particular task is selected, the menu presents user options to control the particular actions associated with the selected task. For example, when a "watch TV" task is selected, the user can be presented options to increase or decrease the TV volume, change the channel, go to an electronic program guide, etc. In a further example, when a "play a DVD" task is selected, the user can be presented options to increase the volume, decrease the volume, play, stop, pause, eject, fast forward, skip to the next section, go to the main menu, etc. It should be noted that each task may routinely involve the control of multiple devices of the home media center, and the particular actions associated with the selected task may require different devices of the home media center to be controlled.

Figures 24, 25:
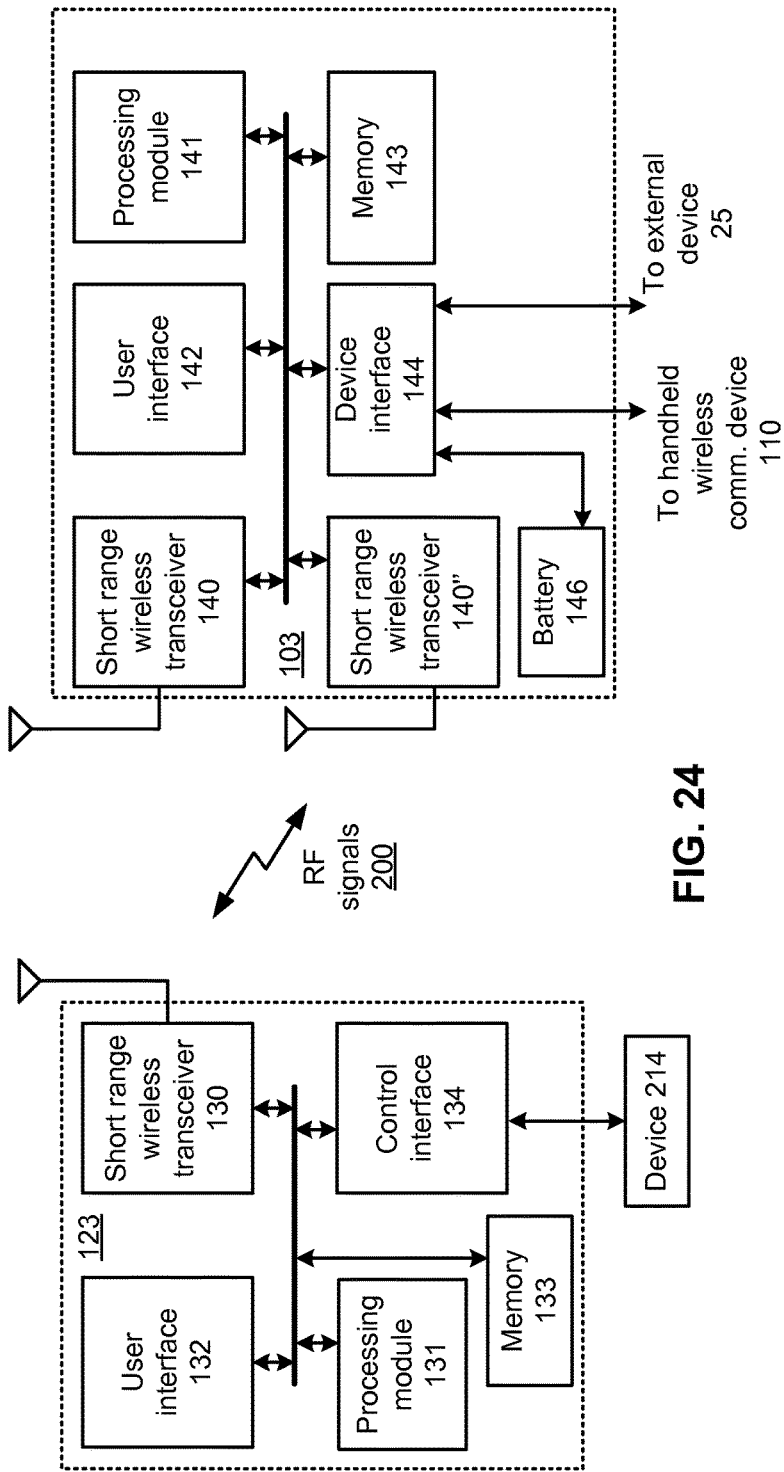
FIG. 24 presents a schematic block diagram of a wireless device 123 and adjunct device 101 in accordance with an embodiment of the present disclosure.
FIG. 25 presents a schematic block diagram of devices 210, 212 and 214 in accordance with an embodiment of the present disclosure.

FIG. 24 presents a schematic block diagram of a wireless device 123 and adjunct device 103 in accordance with an embodiment of the present disclosure. In particular, adjunct device 103 includes each of the components of adjunct device 100 previously described. In addition, the adjunct device 103 includes short-range wireless transceiver 140" that includes a transmitter for RF signals that contain home automation data. Device 123 includes similar components to wireless device 120 but further contains a control interface 134, such as a relay, triac, transistor or other control device for controlling the operation of device 214, such as a lamp or other home lighting, an appliance, a thermostat, or other home device. In an embodiment of the present disclosure, the wireless device 123 is paired with the adjunct device 103 and operates in a similar fashion to a Homelink, Insteon or other home automation device controller to control the operation of an external device 214 in response to RF signals 200 from adjunct device 103.

In an embodiment of the present disclosure, the adjunct device 100 is coupled to a handheld wireless communication device 110 that executes a home automation application for controlling the operation of a device 214. In operation, the device interface 144 receives application data from the home automation application of the handheld wireless communication device 110 via the communication port of the handheld wireless communication device 110. The application data includes control data for controlling the operation of device 214 via wireless device 123. While a single device 214 is shown, the handheld wireless communication device 110 and adjunct device 101 can control a plurality of such devices in a similar fashion. The short-range wireless transceiver 140" generates RF signals 200 based on the control data to control the operation of the device coupled to device 123. The adjunct device 101 and handheld wireless communication device 110 can control the operation of device 214 from a different room or otherwise, while wireless device 123 is in range of RF signals 200.

FIG. 25 presents a schematic block diagram of devices 210, 212 and 214 in accordance with an embodiment of the present disclosure. In an embodiment of the present disclosure device 210 is implemented via adjunct device 103 and handheld wireless communication device 110, and device 212 is implemented via a home automation device controller. In a similar fashion to the system of FIG. 24, device 210 is paired with wireless device 212 to operate in a home automation mode. Control data is transmitted via RF signals 200. Device 212 receives the RF signals 200 and decodes the control data to control device 214.

Figure 26:
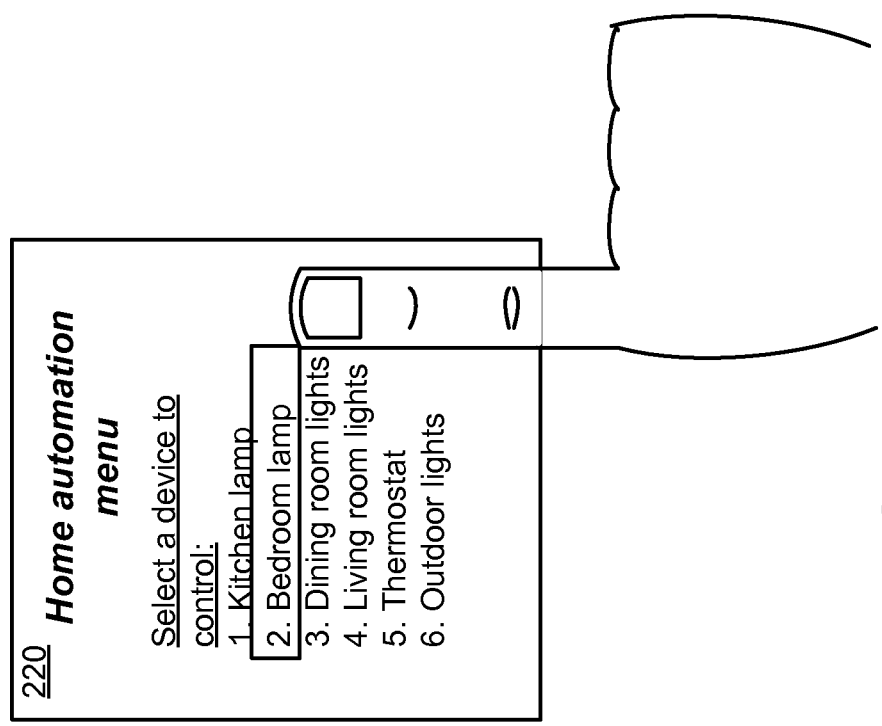
FIG. 26 presents a pictorial representation of a screen display 220 in accordance with an embodiment of the present disclosure.

FIG. 26 presents a pictorial representation of a screen display 220 in accordance with an embodiment of the present disclosure. In particular, a screen display 220 is shown for display via a graphical user interface generated by a home automation application of handheld wireless communication device 110. As shown, the graphical user interface includes a menu that indicates the plurality of devices 214 to be controlled, that each correspond to one of a plurality of devices 212.

In an embodiment of the present disclosure, the pairing procedure described in conjunction with FIG. 25 generates a list that identifies the plurality of devices 212 and the plurality of devices 214. In particular, as a device 212 is paired with the adjunct device 100, the home automation application of handheld wireless communication device queries the user to enter a name of an object or other identifier of the device 214 associated with the device 212 being paired with the adjunct device 100. The names so entered are stored in the list in association with the device identifiers or other address information for the corresponding paired device 212 that is either generated or received during the pairing process.

As shown, the home automation menu is generated based on the list of devices 214—in this case, the devices identified 1-6. The user initiates the control of a device 214 via its wireless device 120 or adjunct device 100, by selecting the assigned name of the device 214 from the menu.

While not shown, the set-up menu may further prompt the user to establish one or more tasks to be performed by one or more devices to be controlled. These tasks might include: watching TV, reading a book, having a party, etc. For each selected task, the application configures the specific remote control operations required to control the devices of the home to states that correspond to the particular task. In the watching TV task, the lights might be dimmed to a particular level, particular lights might be turned on for reading a book. For a party, all of the lights might be turned in areas of the home associated with entertaining while the temperature of the heating and cooling system may be decreased to compensate for the additional heat produced by the guests themselves.

As discussed in conjunction with the remote control application, in addition to task selection, the set-up menu may further prompt the user to establish one or more groups of devices to be controlled, and set up tasks associated with each group. For example, one group of devices might include the living room lighting, a second group of device might include outdoor lighting, a third group of devices might include the home heating/cooling system, etc.

Further, the set-up menu may further prompt the user to establish one or more complex tasks. The operation of lights, TV's, and the like, can be logged over time. This log could be re-played in "vacation-mode" to give a more realistic simulation of being home, compared with the use of timers, not to mention the increased convenience of this method. In addition to remote control and/or home automation devices, the tasks can further involve interaction with one or more remote wireless devices such as remote wireless device 120. For instance, a more complex task might include, turning on an overhead light when a person carrying the remote wireless device enters a room between the hours of x and y, but during other hours illuminate the night light, otherwise turn off all lights.

Figure 27:
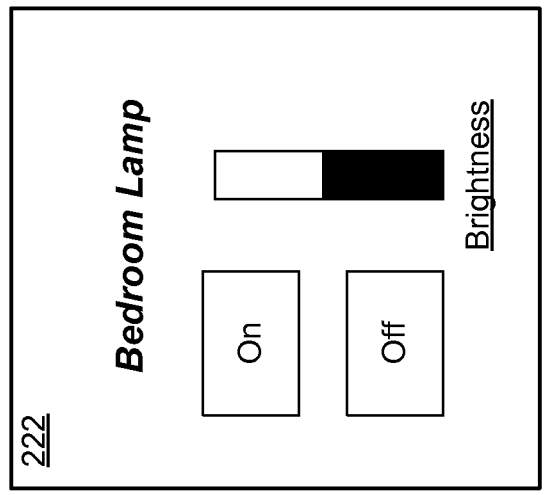
FIG. 27 presents a pictorial representation of a screen display 222 in accordance with an embodiment of the present disclosure.

FIG. 27 presents a pictorial representation of a screen display 222 in accordance with an embodiment of the present disclosure. In particular, a screen display 222 is shown for display via a graphical user interface generated by an application of handheld wireless communication device 110, such as a general paging application. As shown, the graphical user interface includes an identified device 214 "Bedroom Lamp" and interactive controls for controlling the operation of the selected device 214.

In operation, control data is generated by the home automation application is response to the user's interaction with the screen 222. The control data is passed from the handheld wireless communication device to the adjunct device 103 via the communication port and the device interface 144. RF signals 200 containing the control data are generated by short-range wireless transceiver 140" and transmitted to the device 212 for control of the selected device 214.

In an alternative embodiment involving one or more tasks established as described in conjunction with FIG. 26, the screen display be "task oriented" instead of device oriented as shown in FIG. 27. For each selected task, the home automation application configures the screen display of the handheld wireless communication device 110 to implement a menu of the particular home automation commands associated with that particular task. For instance, the user can be presented with a menu of groups that gave been configured. Once a group has been selected, a menu of tasks associated with that group is presented. Once a particular task is selected, the menu presents user options to control the particular actions associated with the selected task.

Figure 28:
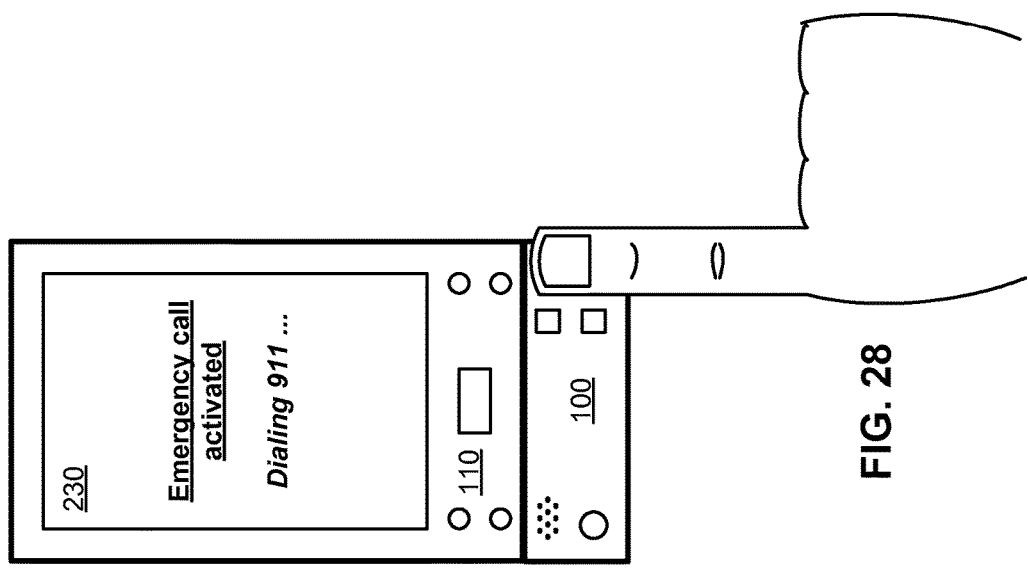
FIG. 28 presents a pictorial representation of handheld wireless communication device 110 and adjunct device 100 in accordance with an embodiment of the present disclosure.

FIG. 28 presents a pictorial representation of handheld wireless communication device 110 and adjunct device 100 in accordance with an embodiment of the present disclosure. In particular, handheld wireless communication device 110 includes a wireless telephony transceiver and further includes a wireless telephony application for sending and receiving telephone calls via the wireless telephony transceiver in communication with a wireless telephony network.

The wireless telephony application receives a 911 signal generated by the adjunct device 100 via the communication port of the handheld wireless communication device 110 and generates the screen display 230 that is shown. In particular, the 911 signal can be generated in response to a user interaction with the user interface 142 of the adjunct device 100—such as by the user pressing an emergency call button on the adjunct device 100. In response to the 911 signal from the adjunct device, the wireless telephony application initiates an emergency call, such as a 911 telephone call, or other emergency call. In addition, emergency call can be initiated to a monitoring service as an alternative to a traditional 911 call. In this fashion, a telephone call such as an automated voice call or other call, SMS message, text message, email or other communication can be initiated to alert the service to an emergency or distress situation. The monitoring service can include an eldercare monitoring service that can respond via its own resources to emergency or distress calls. In addition or in the alternative, the monitoring service can itself initiate a 911 call in response to the receipt of the emergency call from the handheld wireless communication device 110. As will be understood by one skilled in the art, the emergency call, can include location information, such as GPS coordinates or other position information that is relayed to the monitoring service, or the 911 call center to facilitate the location of the handheld wireless communication device 110 that initiated the emergency call.

In this fashion, the user of handheld wireless communication device 110 with adjunct device 100 need only to press a single button on the adjunct device to launch an emergency call, saving time in the event of an actual emergency.

In a further embodiment of the present disclosure, the handheld wireless communication device 110 can initiate an emergency call in response to the activation of a remote wireless device 120, for example, by the user pressing an emergency call button on the remote wireless device 120. In particular, the wireless device 120 transmits a special paging signal, similar to paging signal 16, that includes data or another indication that an emergency call should be initiated. When the adjunct device 100 receives the special paging signal, the adjunct device communicates the 911 signal to the handheld wireless communication device 100 to initiate the 911 call, as if an emergency call button of the adjunct device 100 had been directly pressed by the user as described above.

As discussed in conjunction with FIG. 5, the adjunct device 100 can include a device interface 144 that is switchable between an auxiliary power mode and a battery isolation mode. In the battery isolation mode, the device interface 144 decouples the battery 146 from the battery of the handheld wireless communication device 110, for instance, to preserve the charge of battery 146 for operation even if the battery of the handheld wireless communication device 110 is completely or substantially discharged. In the auxiliary power mode, the device interface 144 couples the power from the battery 146 to the handheld wireless communication device 110 via the communication port to charge the battery of the handheld wireless communication device 110. In an embodiment of the present disclosure, activation of the emergency call feature in the adjunct device 100 can automatically initiate a switch of the device interface 144 to the auxiliary power mode to support emergency calling. In a further embodiment, if the device interface 144 detects a low battery condition during an emergency calling event, the device interface 144 can automatically switch to auxiliary power mode to support emergency calling.

Figure 29:
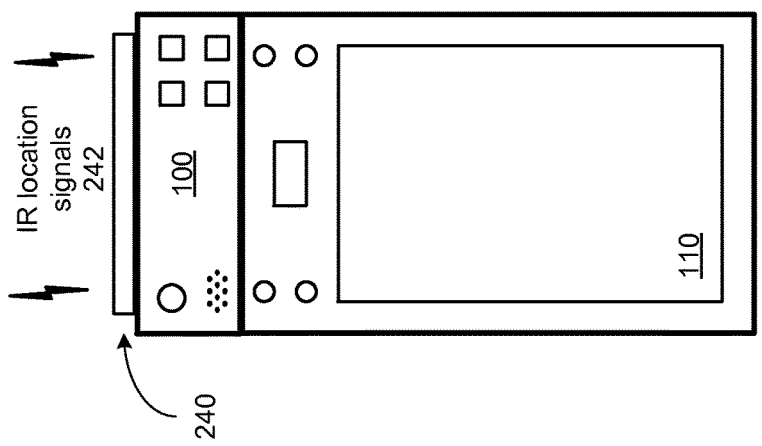
FIG. 29 presents a pictorial representation of handheld wireless communication device 110 and adjunct device 100 in accordance with an embodiment of the present disclosure.

FIG. 29 presents a pictorial representation of handheld wireless communication device 110 and adjunct device 100 in accordance with an embodiment of the present disclosure. In particular, adjunct device 100 includes a plurality of infrared emitters 240 that emit a corresponding plurality of infrared signals, such as IR location signals 242 for use by a sensor coupled to a screen to generate a screen pointer graphic on the display screen. The adjunct device 100 provides feedback to a video device on the position, orientation and or the perspective of the user and/or to otherwise allow the user to interact with a media application on a remote monitor, television or other display device.

The plurality of infrared emitters 240 can be implemented using IR light emitting diodes that emit light with a wavelength of 880 nM, however, other infrared emitters can likewise be used. The plurality of infrared emitters 240 can be arranged in a row, a grid or other pattern to facilitate a remote device to determine the position, orientation and or the perspective of the handheld wireless communication device 110 and/or by inference, the user of the handheld wireless communication device 110.

In an embodiment of the present disclosure, the handheld wireless communication device 110 includes a processor that executes a screen pointer application or other application and wherein the plurality of IR emitters 240 are controlled based on application data from the screen pointer application received by the adjunct device 100 via the communication port of the handheld wireless communication device 110 and device interface 144. In this fashion, the IR emitters 240 can be selectively enabled or disabled. In addition, the IR emitters can be used in conjunction with other applications such as short-range wireless transceiver 140', an infrared data association (IrDA) transceiver or to support other applications of the adjunct device 100 and handheld wireless communication device 110. While a particular form factor for adjunct device 100 is shown, as previously discussed, adjunct 100 can likewise be implemented as a case that encloses a portion of the handheld wireless communication device 110.

Figure 30:
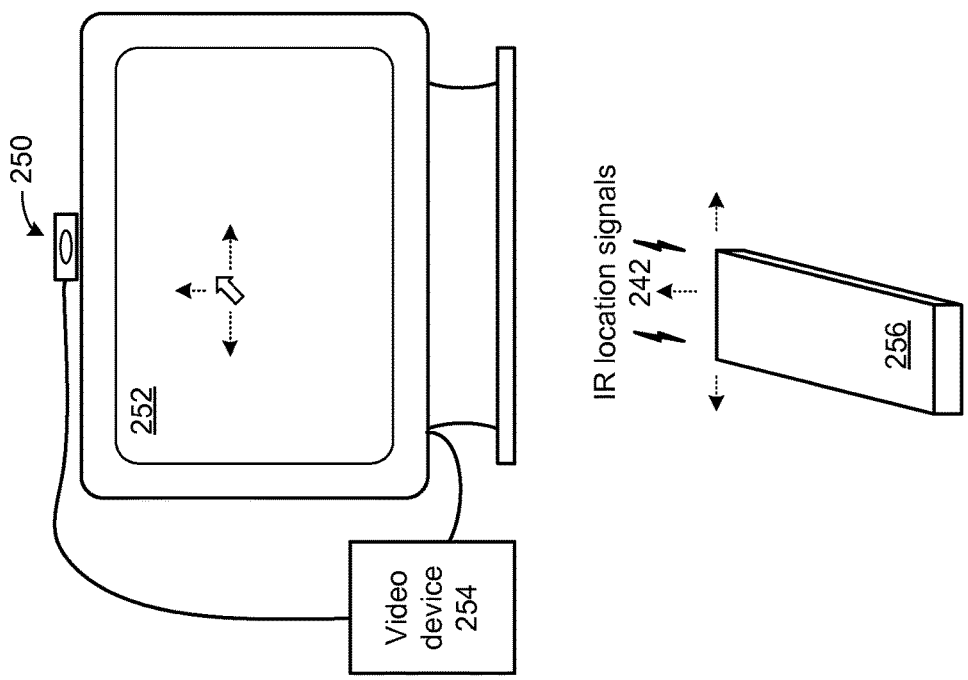
FIG. 30 presents a pictorial representation of screen pointing system in accordance with an embodiment of the present disclosure.

Further examples of this embodiment, including the interoperability between the adjunct device 100 and a display screen are presented in conjunction with FIG. 30 that follows.

FIG. 30 presents a pictorial representation of screen pointing system in accordance with an embodiment of the present disclosure. In particular, a handheld device 256, such as handheld wireless communication device 110 equipped with adjunct device 100 emits IR location signals 242, that are viewed by video camera 250. In an embodiment of the present disclosure, video camera 250 includes a charged coupled device (CCD) array that responds to the infrared location signals 242. In particular, an infrared sensor such as video camera 250 generates a video signal that includes bright spots corresponding to each of the IR emitters 240. In an embodiment of the present disclosure, the video camera 250 includes an infrared filter such as a plastic window injected with an infrared die that allows transmission of infrared light through the window while filtering visible light and other light wavelengths. In this fashion, other light sources can be attenuated providing a clearer video image of the IR emitters 240.

Video device 254 receives the video signal from video camera 250 and analyzes the video signal to determine the position and/or orientation of the IR emitters 240 in the video image. In response, the video device 254 generates a graphical overlay for display screen 252 of the screen pointer that appears on the display screen 252. In this fashion, as the position of the handheld device 256 changes, the position of the screen pointer displayed on display screen 252 changes as well. Further, changes of orientation, such as the rotation of the handheld device 256 about roll, pitch or yaw axes can be detected and used to adjust the orientation of the screen pointer.

In an embodiment of the present disclosure, the video device 254 can include a video game console, computer, set top box, digital video disc player or other video device that operates in conjunction with a display screen 252. While shown as separate elements, the video camera 250 and/or video device 254 can both be incorporated within a display screen 252, such as a television or computer monitor.

It should also be noted that, in other embodiments, the positioning of the video camera 250 and the IR emitters 240 can be reversed. In particular, the plurality of IR emitters 242 can be placed above the display screen 252 and the handheld device 256 can include video camera 250. In the embodiment where handheld device 256 is implemented via handheld wireless communication device 110 and adjunct device 100, the short-range wireless transceiver 140 of adjunct device 100 or other wireless transceiver of adjunct device 100 or handheld wireless communication device 110 can be used to send the video signal produced by the video camera 250 wirelessly to a complementary wireless transceiver included in video device 254.

While the foregoing description has focused on a screen pointer application, other applications including the display of three-dimensional video content including 3D movies or video games can also be adapted to the use of position and directional information of a player or viewer. In particular, in presentations with a single player or viewer, the video content displayed on display screen 252 can be transformed based on the position and/or orientation of the handheld device 256 to present the illusion of a three-dimensional display.

For example, the handheld device 256 can be replaced by an alternative device such as glasses, a hat or other object that tracks the position and/or orientation of a user's head. Objects in the background of either a static or dynamic video image can be shifted up when the user's head moves down, and shifted right when a user's head moves left to provide the illusion, via the two-dimensional display screen, that the user is interacting with a three-dimensional virtual world. It should be noted that such an embodiment can be implemented without polarized or colored lenses or other optical filtering used in conjunction with standard three-dimensional programs.

Figure 31:
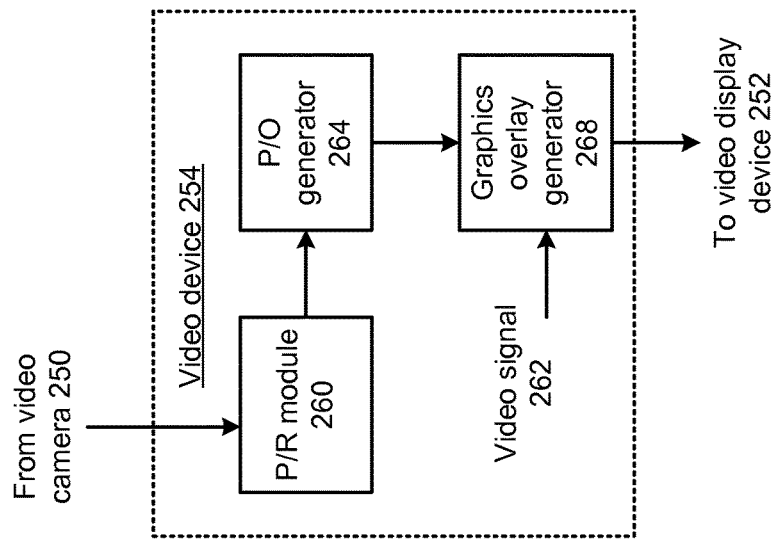
FIG. 31 presents a schematic block diagram of video device 254 in accordance with an embodiment of the present disclosure.

FIG. 31 presents a schematic block diagram of video device 254 in accordance with an embodiment of the present disclosure. In particular, video device 254 includes pattern recognition module 260, position/orientation generator 264, and graphics overlay generator 268. In operation, video device 254 receives the video signal from video camera 250. Pattern recognition module 260 analyzes frames of the video image to recognize the line, grid or other pattern of the IR emitters 240 in the frames, based on the bright spots produced by IR location signals 242.

After the bright spots produced by IR location signals 242 are located, position/orientation sensor 264 generates position and/or orientation signals corresponding to, for instance, x, y, and z-axis translations and roll, pitch and yaw axis orientations of the handheld device 256. These position and/or orientation signals are presented to graphics overlay generator 268, that generates a graphic, such as a screen pointer graphic, curser, icon or other graphic corresponding to the position and/or orientation determined by position/orientation generator 264. In addition, graphics overlay generator 268 overlays the generated graphic on video signal 262 to generate a video output signal to display device 252. The video input signal can be a locally generated video input signal in embodiments where the video device 254 is a video game console, computer, set top box, digital video disc player or other video device generates its own video signals. In the alternative, video signal 262 can be coupled from an external source such as a video game console, computer, set top box, digital video disc player or other video device that operates in conjunction with a display screen 252.

The video signal from video camera 250, video signal 262 and the video output to video display device 252 can each be analog or digital video signals. While not expressly shown, video device 254 can include one or more video decoders, video encoders or video transcoders for converting the video format, frame rate and/or resolution of the video signal from video camera 250, video signal 262 and the video output to video display device 252 for processing in conjunction with video device 254.

In the embodiment discussed in conjunction with FIG. 30 where position and orientation information is used to present the illusion of three-dimensions, video device 254 can include a transformation generator in place of graphics overlay generator 268. In particular, the transformation generator can transform the video signal 262, based on the position and/or orientation determined by position/orientation generator 264 to present a video output signal that video display device 252 that presents the illusion of three-dimensions, without the need for polarized or colored lenses or other optical filtering.

The components of video device 254 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory. Note that when the components of video device 254 implement one or more functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Video device 254 can include additional components that are not expressly shown.

Figure 32:
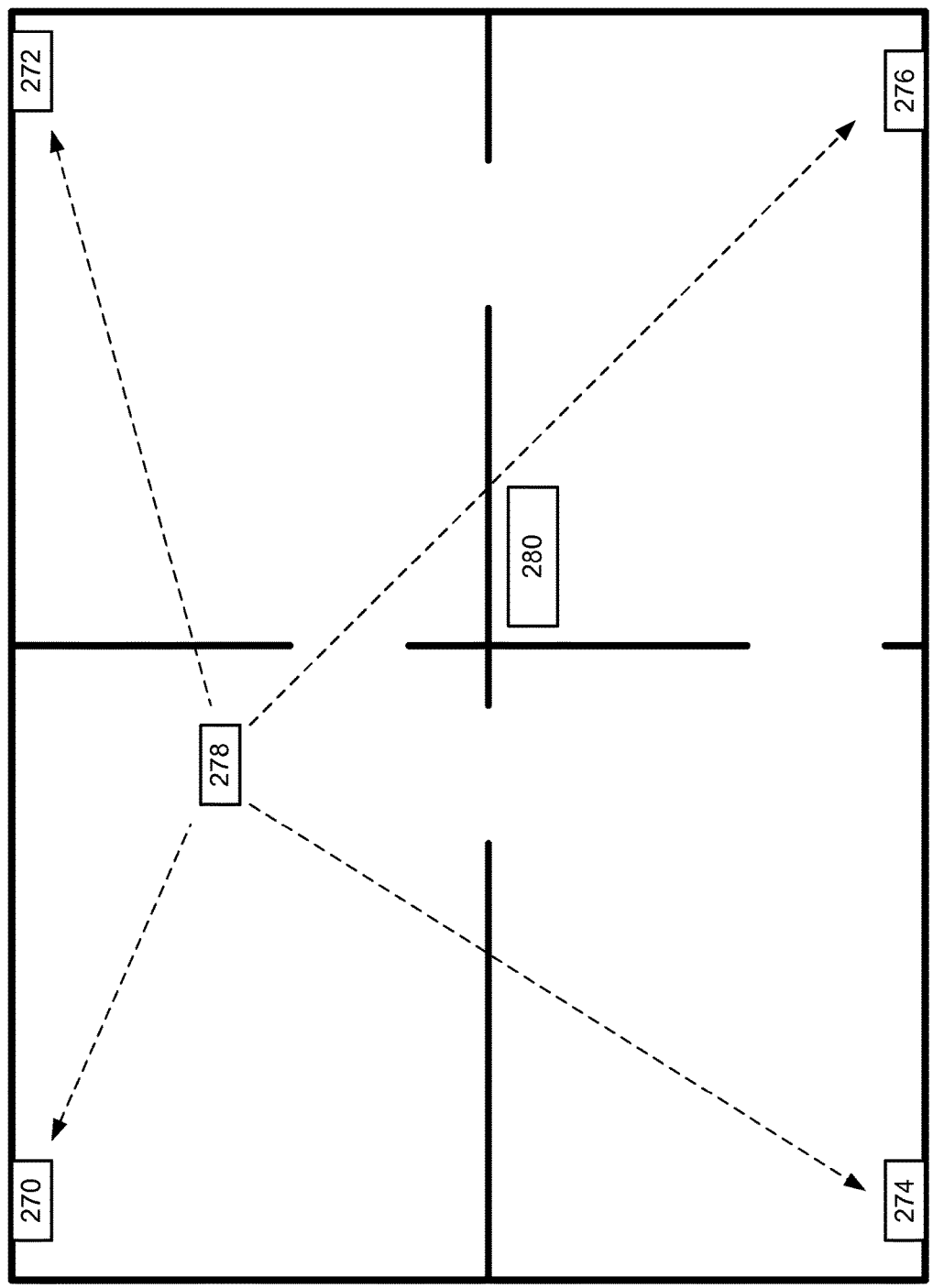
FIG. 32 presents a schematic block diagram representation of a location system in accordance with an embodiment of the present disclosure.

FIG. 32 presents a schematic block diagram representation of a location system in accordance with an embodiment of the present disclosure. In particular, a layout is shown of a building that includes a plurality of paging devices 270, 272, 274, 276, 278 and 280 that have been paired together to form a paging network. Each of the paging devices 270, 272, 274 and 276 is a stationary device that is positioned in a fixed location, such as being attached to a wall or ceiling, or placed in another location that is stationary. The paging devices 270, 272, 274 and 276 can each be implemented, for instance, via any of the embodiments of wireless device 120. The paging device 278 is a mobile paging device to be located. In particular, paging device 278 can be implemented via either any of the embodiments of wireless device 120 or adjunct device 100 and handheld wireless communication device 110.

After these devices have been paired, the mobile paging device 278 can be located as follows. A paging signal, such as paging signal 16 or 112 is transmitted to the paging device 278 by paging device 280. The paging device 280 can either be a fixed paging device or mobile paging device having a short-range wireless transmitter capable of transmitting such a paging signal—such as any of the embodiments of wireless device 120 or adjunct device 100 and handheld wireless communication device 110. In an embodiment of the present disclosure, the paging signal includes a broadcast listen command. The broadcast listen command can, for example, instruct the fixed paging devices 270, 272, 274 and/or 276 to beginning listening for a location signal from the device to be located. In response to the paging signal, the mobile paging device 278 generates the location signal, such as location signal 114 or other location signal generated by an adjunct device 100.

The location signal is received by one or more of the fixed paging devices 270, 272, 274 and/or 276. In response, the fixed paging devices 270, 272, 274 and/or 276 that received the location signal generate location information that is transmitted to the paging device 280. The paging device 280 receives location information pertaining to the mobile paging device 278 via its short-range wireless receiver. In response, the paging device 280 determines a location of the mobile paging device 278 based on the location information.

In an embodiment of the present disclosure, the location information includes directional information gathered by one or more of the fixed paging devices 270, 272, 274 and/or 276 that describe a direction between that fixed paging device and the mobile paging device 278. When directional information is received by two or more of the fixed paging devices 270, 272, 274 and/or 276, the paging device 280 can triangulate the position of the mobile paging device in two dimensions, based on the directional information.

In an embodiment of the present disclosure, the fixed paging devices are each implemented via a wireless device 120 that includes an antenna 138, such as antenna 148' that is programmable. In this embodiment, wireless device 120 operates in a similar fashion to adjunct device 100 and handheld wireless communication device 110 described in conjunction with FIGS. 7-15 to locate a remote paging device that is transmitting a location signal, such as location signal 112.

For example, the processing device 131 of a particular fixed paging device 270, 272, 274 or 276, generates control signals 163 to scan a null or lobe of the programmable antenna 148' over different orientations, determines signal strengths corresponding to the different orientations and determines a direction $\theta_1$, between the particular fixed paging device and the mobile paging device 278, based on a lowest or highest signal strength M, lowest or highest differential signal strength $D(\theta_1)$, etc. Each such fixed paging device 270, 272, 274 or 276 generates directional information that indicates the direction $\theta_1$, and transmits this data to the paging device 280 for analysis. In an embodiment of the present disclosure, the paging device 280 stores the position of each of the fixed paging devices 270, 272, 274 and 276, and uses this information in conjunction with each of the received directions $\theta_1$, to triangulate the location of the mobile paging device 278.

In another embodiment of the present disclosure, the fixed paging devices 270, 272, 274 and 276 generate location information that includes signal strength information of the received location signal from mobile paging device 278. The fixed paging devices 270, 272, 274 and 276 transmit this information to the paging device 280. In response, the paging device 280 determines which of the fixed devices 270, 272, 274 and 276 has the greatest signal strength. In this fashion, the paging device can infer that the mobile paging device 278 is closest to the fixed paging device 270, 272, 274 or 276 having the greatest signal strength.

It should be noted that the handheld wireless communication device 110 can include an internal compass that generates an indication of its own orientation. This orientation information can also be used in conjunction with the received directions $\theta_1$, to triangulate the location of the mobile paging device 278 or provide absolute directional information.

The location system of FIG. 32 enables many interesting applications. For example, a restaurant can be equipped with a plurality of fixed paging devices that are paired with a plurality of mobile paging devices and a master console that operates as paging device 280. When a customer enters the restaurant, he or she is assigned a mobile paging device, such as mobile paging device 278. The master console can be used to page the mobile paging device when a table is ready. When the customer is assigned a table, the customer continues to use the mobile paging device 278. For instance, the mobile paging device 278 can be used to initiate pages to the master console to place an order or supplement an existing order, to request a server, etc. In conjunction with these activities, the location system provided by the fixed paging devices can be used to locate the mobile paging device, correlate the location to a table and server, locate a lost paging device, etc.

In other applications, the location system of the present disclosure can be used in conjunction with the location of persons in hospitals, nursing homes and hospices; the location of files or records in an office building; or the location of boxes or inventory in a warehouse or manufacturing facility or for a host of other applications. In pertinent part, the mobile paging device 278 is constructed with a form factor that can be enclosed in or attached to an object, person or other thing to be located.

It should be noted further that the applications described above can alternatively be implemented without the use of a fixed network of paging devices. A remote wireless device 120 or adjunct device 100 can be associated with each table via a table ID or other data structure. A notebook computer, wireless telephone, iPad device other handheld wireless computing device 110 can be paired with and used to receive pages or other signaling to monitor each of the remote wireless devices 120 and overlay information on a map or other layout of the restaurant's layout. This provides a simpler implementation without the need of a plurality of fixed paging devices. In this case, the table ID provides the location information used to identify the table associated with each mobile device.

It should be specifically noted that the emergency monitoring functionality described in conjunction with FIG. 28 can be combined in the implementations above for applications in a hospital, hospice, nursing home or other care facility. Location and tracking information gathered as described above can be combined with emergency calling to a monitoring center or other emergency messaging to inform a monitoring center of an emergency event and further to provide enhanced location information.

In a further embodiment, accelerometer information from the handheld wireless communication device 110, such as an iPhone can be used to trigger an emergency call. For example, if a period of inactivity is detected based on a lack of motion over an inactivity period, such as 30, 60, or 90 minutes, a fail-safe distress call can be initiated to the monitoring center to check on the person associated with the device.

While the foregoing description has focused on emergency calling, other automatic calling and alerts can also be implemented in accordance with various implementations of the present disclosure. In particular, the pairing procedure described in conjunction with FIG. 18 can be expanded to set-up additional options such as those described below.

1) If Sue's phone is not located at home at a particular time (such as when Sue should be home from school in the afternoon), as determined by proximity to one or more fixed paging devices 270, 272, 274, 276, etc., initiate a text message, email, telephone call or other communication to Mom's phone.
2) If Sue's phone initiates a 911 call, automatically broadcast a paging signal 112 to all remote devices 120.
3) If Sue's phone initiates any telephone call or text message after 11:00 pm at night, initiate a paging signal to Mom's phone that indicates a call or text message and the destination number.

As discussed in conjunction with FIG. 20, the RF implementation of short-range wireless transceivers 130' and 140' can be used for other uses. In an embodiment of the present disclosure, distress signals, emergency calling signals and other automatic messages and alerts can be transmitted to a home computer via a Bluetooth or 802.11 connection and relayed indirectly to the handheld wireless communication device 110 via the internet, wireless local area network and/or the long range wireless transceiver of the handheld wireless communication device 110.

Figure 33:
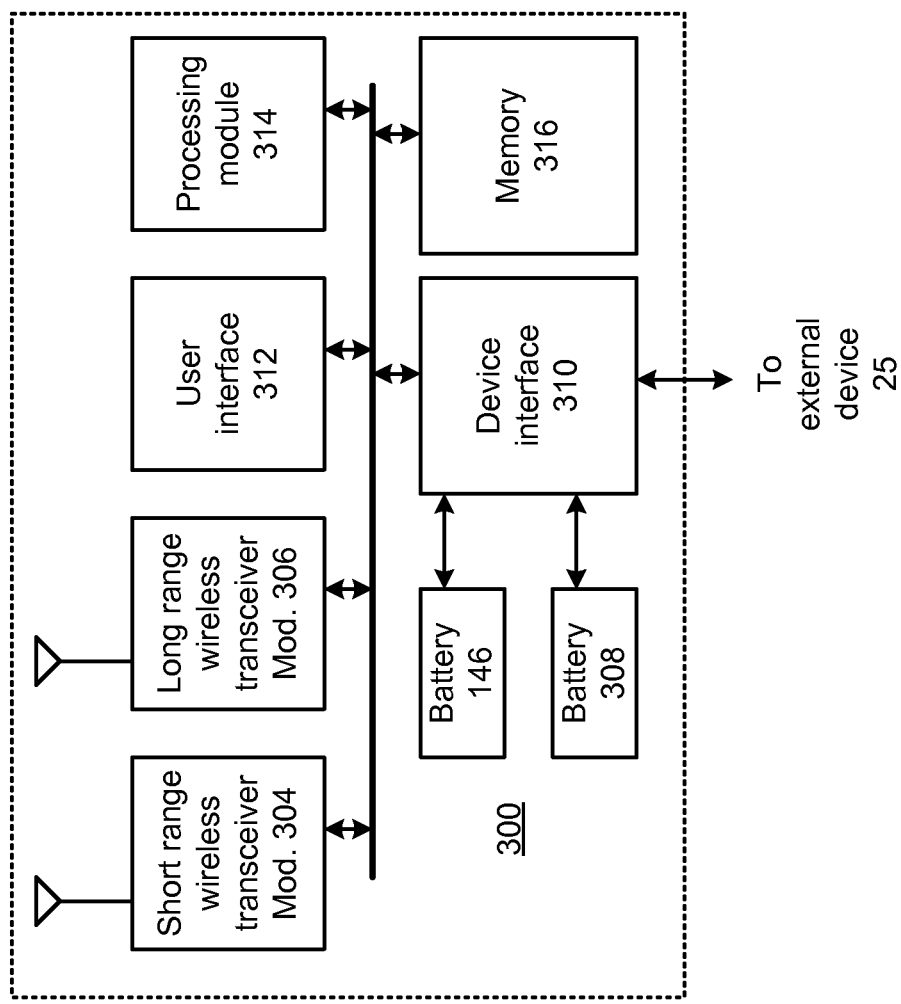
FIG. 33 presents a schematic block diagram of a handheld wireless communication device 300 in accordance with an embodiment of the present disclosure.

FIG. 33 presents a schematic block diagram of a handheld wireless communication device 300 in accordance with an embodiment of the present disclosure. While many of the descriptions of the present disclosure contained herein focus on functions and features ascribed to an adjunct device operating in conjunction with a handheld wireless communication device, the functions and features of the adjunct device handheld wireless communication device combination can be implemented in an enhanced handheld wireless communication device that includes structure and functionality drawn from an adjunct device, such as adjunct devices 100, 100', 101 and 103. Handheld wireless communication device 300 presents such a device that includes a handheld wireless communication device portion having the standard components of a handheld wireless communication device and an adjunct portion that adds the components necessary to provide the additional functions and features of the adjunct device 100, 100', 101 and 103. In summary, handheld wireless communication device 300 includes the structure and functionality of any of the embodiments of handheld wireless communication device 110 and adjunct device 100, 100', 101 and 103, within a single housing, and without the external connections required to couple adjunct device 100, 100', 101 or 103 to handheld wireless communication device 110.

In particular, handheld wireless communication device 300 includes long range wireless transceiver module 306, such as a wireless telephony receiver for communicating voice and/or data signals in conjunction with a handheld wireless communication device network, wireless local area network or other wireless network. In addition, handheld wireless communication device 300 includes a user interface 312 that include one or more pushbuttons such as a keypad or other buttons, a touch screen or other display screen, a microphone, speaker, headphone port or other audio port, a thumbwheel, touch pad and/or other user interface device. User interface 312 includes the user interface devices ascribed to handheld wireless communication device 110 and further provides the functionality and/or structure of the user interface devices 142 described in conjunction with adjunct device 100, 100', 101 and 103.

Handheld wireless communication device 300 includes a main battery 308 that operates in a similar fashion to the battery of handheld wireless communication device 110, while a separate battery 146 provides the functions and features described in conjunction with adjunct device 100, 100', 101 and 103. For example, in isolation mode, battery 146 provides power to the adjunct portions of handheld wireless communication device 300, while main battery 308 provides power to the wireless telephony portions of the handheld wireless communication device 300. Device interface 310 functions as device interface 310 without, however, an internal communication port and plug connection between the adjunct device 100 and handheld wireless communication device 110. Short-range wireless transceiver module 304 includes one or more short-range wireless transceivers such as short-range wireless transceivers 140, 140', 140", etc.

The handheld wireless communication device 300 includes a processing module 314 that operates in conjunction with memory 316 to execute a plurality of applications including a wireless telephony application and other general applications of the handheld wireless communication device and other specific applications described in conjunction with the operation of adjunct device 100, 100', 101 and 103 and handheld wireless communication device 110.

The processing module 314 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 316. Note that when the processing module 314 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 316 stores, and the processing module 314 executes, operational instructions corresponding to at least some of the steps and/or functions illustrated herein.

The memory module 316 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of handheld wireless communication device 300 are shown as being coupled by a particular bus structure, other architectures are likewise possible that include additional data busses and/or direct connectivity between components. Handheld wireless communication device 300 can include additional components that are not expressly shown.

Further, while the present disclosure has been described in conjunction with a handheld wireless communication device 300 or 110, it should be noted that the functions and features of the present disclosure can be implemented in conjunction with an adjunct device coupled to another mobile or stationary computing device capable of executing one or more of the applications described herein in conjunction with handheld wireless communication device 110 or in an another integrated device that includes one or more functions and features of adjunct device 100, 100', 101 and 103 and handheld wireless communication device 110.

FIG. 34 presents a pictorial representation of a back view of an adjunct device 330 in accordance with an embodiment of the present disclosure. In particular, adjunct device 330, such as adjunct device 100, 100', 101 and/or 103, is implemented as a case for an Apple iPhone, iPod or iTouch device. The case includes a camera hole for the camera of the iPhone, an external device connector 334, such as communication port 28' implemented as a micro-USB port. An audio port 336 is included for a beeper, buzzer or other sound emitter included in user interface 142. IR port 332 is included for coupling to the emitters/detectors of short-range wireless transceiver 140', IR emitters 240, or a video camera that operates in an embodiment of FIGS. 29-30, where the IR emitters are mounted in association with the display screen 252.

FIG. 35 presents a pictorial representation of a cutaway side view of an adjunct device 330 in accordance with an embodiment of the present disclosure. As shown, the adjunct device 330 includes a connector 340, that operates in a similar fashion to plug 26 to couple the adjunct device 330 to the communication port of the Apple iPhone, iPod or iTouch device. The case is constructed of a flexible plastic or other flexible material so as to be clipped onto the iPhone, iPod or iTouch device, while enclosing the back, sides, top and bottom of the iPhone, iPod or iTouch device, yet leaving open substantially all of the front to allow the user to interact with the touch screen and optionally the front panel button of the device. Internal components 338 include the components of adjunct device 100, 100', 101 and/or 103. The internal components 338 can include one or more flexible circuit boards to support the flexibility of adjunct device 330, without damage to the components of adjunct device 330.

While not expressly shown, the adjunct device 330 includes one or more other ports to provide user access to the headphone jack, power button, speaker and microphone of the iPhone, iPod or iTouch device. While the adjunct device 330 is shown as a case for an Apple iPhone, iPod or iTouch device, similar adjunct devices are possible for use with other handheld wireless communication devices and handheld devices in accordance with the present disclosure.

Figure 36:
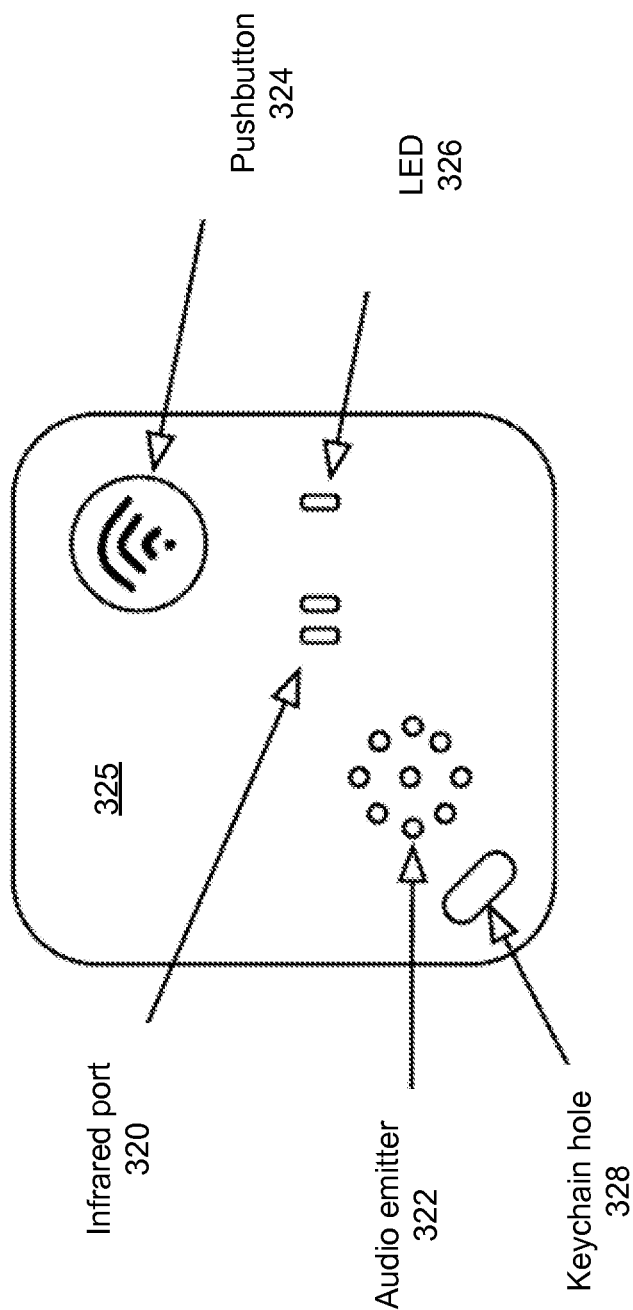
FIG. 36 presents a pictorial representation of a front view of a wireless device 325 in accordance with an embodiment of the present disclosure.

FIG. 36 presents a pictorial representation of a front view of a wireless device 325 in accordance with an embodiment of the present disclosure. In particular, a wireless device 325, such as wireless device 120, 122 or 123, includes a keychain hole 328. In addition, wireless device 325 includes audio emitter 322, LED 326 and pushbutton 324 that are included in user interface 132. Infrared port 320 is coupled to an infrared wireless transceiver, such as short-range wireless transceiver 130'. While not shown, the wireless device 325 includes a back connector interface for connection to an external charger for charging an internal rechargeable battery.

As previously discussed, the wireless device 325 can be implemented using a ZigBee short-range wireless transceiver that operates in conjunction with the RF4CE standard. When the button is pressed and released on a wireless device 325, a broadcast message will be sent to all devices in its paging network. Paging commands can use the NLDE-Data request primitive as described in section 3.1.1.1 of the RF4CE specification with the TxOptions: Broadcast, IEEE Address, Acknowledged, Security on, Single Channel, Specify. A broadcast message can optionally be sent from the adjunct 330 as well, or specific items can be paged. If specific items are targeted, then the PairingRef field is specified, and "broadcast" in the TxOptions field is not enabled. The remainder of the data service messaging can proceed as specified in section 3.1.1 of the RF4CE specification.

The wireless device 325 can be paired with similar devices as well as adjunct device 100, 100', 101, 103 or 330 as set forth in the RF4CE standard. Two such wireless devices 325 can implement a pairing procedure that includes, for instance, pressing and holding down the pushbutton 324 or some other button, such as a small recessed button of both devices for at least four seconds. When they are paired with each other, they will both chirp twice via sound emitter 322 and the LED 326 will stop flashing. Pairing can be cleared by pressing and holding the pushbutton for 8 seconds. Clearing can be acknowledged by a single chirp via sound emitter 322 and the flashing of LED 326. Other compatible devices can be configured for pairing or cleared in a similar fashion, however, the user interface of handheld wireless communication device 110 can optionally be used to assist the pairing process.

In operation, when the pushbutton on one unit is depressed, all the other units in the same paging network can emit a loud alarm via audio emitter 322, flash a light such as LED 326, etc. In one example of operation, a user may purchase a wireless device 325 that he puts on his key ring and one in his wallet. If the user misplaces his wallet but has his keys in his pocket, he simply pages his wallet using the key ring wireless device 325, or vice versa. A very forgetful person may buy one more wireless device 325, so he had two for the keys and the wallet and one more stuck on the wall next his bed. If both the keys and wallet are lost he pushes the wireless device 325 next to his bed and the buzzer sounds on both items.

In a further example, a mother of five children in a supermarket may put one wireless device 325 in the pocket of each child to retrieve them should they wander off Wireless device 325 can be programmed to send signals such as periodic beacons or polling signals to determine if all other wireless devices 325 are present in the network. In this fashion, a wireless device 325 can be programmed to sound an alarm if a child wanders outside of a certain range, based on lack of a response to a poll, low signal power, etc. As previously discussed, the adjunct device 330 can operate as a wireless device 325 in any of the examples discussed above.

As discussed in conjunction with FIGS. 20-23, wireless device 325 can respond to wireless commands from an adjunct device 330, to relay infrared commands to other wireless device 325 of other devices to be controlled. So, a user can tape a tag on the inside door of a home entertainment system and control that system from places that are not possible with standard infrared remotes. The system can be used to control multiple TVs or entertainment centers within the same home or across multiple sites based on a user selected group of devices and/or selected tasks including complex tasks based on, for example, GPS position information, time of day, compass direction, distance and other parameters.

As discussed in conjunction with FIGS. 24-27, a user can replace their existing garage door opener button with a wireless device 325 and control their garage door from their handheld wireless communication device via an adjunct device 330. Since many smartphones have GPS, this would allow intelligent handheld wireless communication device applications such as automatically opening the garage door as the user drives up. Home lighting can be similarly controlled, where the lights in the house automatically turn off if there is no wireless device 325 or adjunct 330 present in the home.

As previously discussed a wireless device 325 will be able to function as both a pager and IR relay device at the same time. The network topology for IR Relay devices is slightly different, however. Where the paging function was performed among peers, IR relay can operate based on a master-slave relationship between the adjunct device 330 and the wireless device 325. Multiple adjunct devices 330 can control a single wireless device 325 and one adjunct device 330 can control many wireless devices 325.

In an example of operation, three wireless devices 325 are set up in various places for IR relay, one in front of the TV, one inside a cabinet in front of the DVD and VCR, and a third on the other side of the room where the CD player sits. Each has its own network for IR relay. Both Mom's iPhone and the teenager's iPhone (via corresponding adjunct devices 330) can control all three devices. The adjunct devices 330 can initiate data delivery.

To save power, wireless devices 325 may only be awake a small percentage of the time during in a standby mode of operation. For example, a wireless device 325 may typically be awake to transmit and receive a small amount of time every two or more seconds while waiting for a command.

The wireless devices 325 can switch itself to an active state when a command or other signaling is received from another device. For instance, following the example discussed above, the adjunct device 330 can send to the target wireless devices 325 the RX-ENABLE.request signal for a reasonable active period such as 5 seconds, to wake up the device and keep it awake for a period of time. After that, the adjunct device 330 can transmit codes such as commands and other control data.

FIG. 37 presents a flowchart representation of a method in accordance with an embodiment of the present disclosure. In particular, a method is presented for use in conjunction with one or more functions and features described in FIGS. 1-36. In step 400, data is generated to present for display on a handheld wireless communication device a graphical user interface that receives an indication of a user to locate at least one personal object and that generates a location signal in response thereto. In step 402, the location signal is communicated to an adjunct device via the communication port of the handheld wireless communication device to cause the adjunct device to transmit an RF paging signal to at least one remote wireless device via a short-range wireless transceiver of the adjunct device.

In an embodiment of the present disclosure, the at least one personal object includes a plurality of personal objects and the at least one remote wireless device includes a plurality of remote wireless devices. The graphical user interface can include a menu that indicates the plurality of personal objects. The indication of the user to locate the at least one personal object can include a selected one of the plurality of personal objects. The location signals can indicate a corresponding one of the plurality of remote wireless devices.

The method can also include a pairing procedure for pairing the adjunct device with the plurality of remote wireless devices. The pairing procedure can generate a list that identifies the plurality of remote devices and the plurality of personal objects. The menu that indicates the plurality of personal objects can be generated based on the list.

In an embodiment of the present disclosure the remote device can generate a location signal in response to the paging signal. The adjunct device can include a directional antenna, coupled to the short-range wireless receiver. The short-range wireless receiver of the adjunct device can generate a signal strength in response to the location signal. The homing application can further include receiving the signal strength via the communication port and the graphical user interface can further generate a signal strength indication to the user. The directional antenna can have a reception pattern that includes a null.

In an embodiment of the present disclosure, a time of flight can be used instead of or in addition to signal strength to determine the distance to a remote device. In particular, the time can be measured from the transmission of the paging signal to the reception of the location signal. This time delay (round trip flight time) can indicate the distance to the remote device. The time delay, $T_d$, can be represented as follows:

$$T_d = T_{f1} + T_{f2} + T_p$$

where, $T_p$ represents the processing time to generate the location signal in response to the paging signal and to recognize the location signal, $T_{f1}$ represents the flight time for the paging signal to travel to the remote device and $T_{f2}$ represents the flight time for the location signal to travel from the remote device to the adjunct device. Considering the processing time $T_p$ to be fixed, the distance to a remote device, $D_{ft}$, can be approximated based on the following:

$$D_{ft} = c(T_f) = c(T_d - T_p)$$

where is c is a proportionality constant that is based on the speed of light in air and $T_f = (T_{f1} + T_{f2})$.

It should be noted that signal strength and flight time and both be considered in estimating the distance to a remote device. Consider for example, a distance measurement can be expressed as a function $f$ of signal strength, $D_{ss}$, as follows:

$$D_{ss} = f(RSSI)$$

where RSSI is a received signal strength indication. A final distance measurement D can be determined based on either:

$$D = g(D_{ft}, D_{ss})$$

or $$D = h(T_f, RSSI)$$

where g and h are either linear or nonlinear functions. For example, distance can be calculated both ways and averaged to determine a more refined measurement. In a further example, the difference between the two measurements can be used to determine a relative accuracy of the distance estimate.

It should be noted that he functions g or h can be generated to determine distance differently under different conditions. For example, for longer distances determined for instance by either a value of $T_f$ that is above a high flight time threshold and/or a RSSI below a low signal strength threshold, the distance D can be estimated either exclusively based on either $T_f$ or $D_{ft}$ or by predominately weighting the values of $T_f$ or $D_{ft}$ in combination with $D_{ft}$ or RSSI. Further, for midrange distances determined for instance by either a value of $T_f$ that is below a high flight time threshold, but above a low flight time threshold and/or a RSSI above a low signal strength threshold and below a high signal strength threshold, the distance D can be estimated based on a more equal weighting of the values of $T_f$ or $D_{ft}$ in combination with $D_{ft}$ or RSSI. In addition, for shorter distances determined for instance by either a value of $T_f$ that is below a low flight time threshold and/or a RSSI above a high signal strength threshold, the distance D can be estimated either exclusively based on either $D_{ft}$ or RSSI or by predominately weighting the values of $D_{ft}$ or RSSI in combination with $T_f$ or $D_{ft}$. In this fashion, greater importance can be attributed to high values of RSSI and/or $T_f$.

FIG. 38 presents a flowchart representation of a method in accordance with an embodiment of the present disclosure. In particular, a method is presented for use in conjunction with one or more functions and features described in FIGS. 1-37. In step 410, data is generated to present for display on the handheld wireless communication device a graphical user interface that receives an indication of a user to control at least one home device and that generates a control signal in response thereto. In step 412, the control signal is communicated to an adjunct device via the communication port of a handheld wireless communication device to cause the adjunct device to transmit a wireless signal to at least one wireless interface via a short-range wireless transmitter of the adjunct device.

In an embodiment of the present disclosure, the home devices can include a plurality of home devices, each of the plurality of home devices having a wireless interface. The graphical user interface can include a menu that indicates the plurality of home devices and the indication of the user to control the home device can include a selected one of the plurality of home device. The control signal can indicate a corresponding one of the plurality of home devices.

In an embodiment of the present disclosure, the remote control application further includes a pairing procedure for pairing the adjunct device with the plurality of home devices. The pairing procedure can generate a list that identifies the plurality of home devices and the menu that indicates the plurality of home devices can be generated, based on the list. Home devices can include a home automation device or a home media device. The short-range wireless transmitter can include an infrared transmitter.

FIG. 39 presents a flowchart representation of a method in accordance with an embodiment of the present disclosure. In particular, a method is presented for use in conjunction with one or more functions and features described in FIGS. 1-38. In step 420, a 911 signal generated by an adjunct device is received via a communication port of the handheld wireless communication device. In step 422, a 911 call is initiated via the wireless telephony transceiver in response to the 911 signal. As discussed in conjunction with FIG. 28, the emergency call can include location information, such as GPS coordinates or other position information that is relayed to a monitoring service, or a 911 call center to facilitate the location of the handheld wireless communication device 110 that initiated the emergency call.

FIG. 40 presents a flowchart representation of a method in accordance with an embodiment of the present disclosure. In particular, a method is presented for use in conjunction with one or more functions and features described in FIGS. 1-39. In step 430, a plurality of paging devices are paired to form a paging network, the plurality of paging devices including a plurality of fixed paging devices and the mobile paging device. In step 432, a paging signal is transmitted to the plurality of paging devices via a short-range wireless transmitter. In step 434, location information is received via a short-range wireless receiver pertaining to the mobile paging device from at least one of the plurality of fixed paging devices. In step 436, a location of the mobile paging device is determined based on the location information.

In an embodiment of the present disclosure, the location information includes directional and distance information between the at least one of the plurality of fixed devices to the at least one mobile device and wherein determining the location of the at least one mobile device includes a triangulation of the directional information. The method can further include receiving a location signal, at the at least one of the plurality of fixed paging devices; scanning a programmable antenna in the at least one of the plurality of fixed paging devices to determine signal strengths corresponding to a plurality of null directions; determining a lowest of the signal strengths; and determining the directional information based on the one of the plurality of null directions corresponding to the lowest of the signal strengths. In this method, the paging signal can be transmitted via a handheld wireless communication device or via an adjunct device coupled to a handheld wireless communication device or other device.

In an embodiment of the present disclosure, the location information includes signal strength information and step 436 includes: determining the at least one of the plurality of fixed devices having the greatest signal strength; and determining a proximity to the at least one of the plurality of fixed devices having the greatest signal strength.

As previously discussed, distance can be determined based on a time of flight methodology that looks to round trip signal delay to determine a measure of distance to a remote device.

While the description above has set forth several different modes of operation, the devices described here may simultaneously be in two or more of these modes, unless, by their nature, these modes necessarily cannot be implemented simultaneously. While the foregoing description includes the description of many different embodiments and implementations, the functions and features of these implementations and embodiments can be combined in additional embodiments of the present disclosure not expressly disclosed by any single implementation or embodiment, yet nevertheless understood by one skilled in the art when presented this disclosure.

FIG. 41 presents a block diagram representation of wireless device in accordance with an embodiment of the present disclosure. In particular a wireless device 500 is presented, such as any of the wireless device 100, 120 and 300, etc. previously described. As previously discussed, the generation of location signals between devices can be used to determine if two devices are in proximity to one another.

For example, multiple devices can be associated with different people and the location signals received by a wireless device from other wireless devices can be used to indicate which of these devices and associate people are present at a particular location.

In this fashion, wireless device 500 can determine which people or devices are in its proximity, or not in its proximity.

In the embodiment shown, the wireless device 500 includes a processor 502, memory 504, user interface 506 and short-range wireless transceiver 508. In operation, the user interface 506 generates a pairing signal in response to an indication from a user to associate the wireless device with a plurality of mobile communication devices in proximity to the wireless device. A short-range wireless transceiver 508 is configured to communicate RF signals, in response to the pairing signal from the user, including a beacon signal to identify the wireless device 500 and to facilitate the association of the wireless device 500 with the mobile communication devices in proximity to the wireless device 500 such as tablet computer 510, personal computer 512, wireless phone 514, smart watch or other wearable communication device 516. For example, the mobile communication devices can include at least one first mobile communication device operating via a first operating system such as Apple iOS, and at least one second mobile communication device operating via a second operating system such as an Android or Windows operating system. The short range wireless transceiver can communicate via a network 525 in accordance with a Bluetooth protocol, a Zigbee protocol, an 802.11 protocol or other wireless communication protocol. Each of the mobile communication devices includes its own processor and memory and a corresponding short range wireless transceiver that allows the mobile communication device to communicate with the wireless device 500.

The processor of each mobile communications device executes an application that facilitates location of the corresponding mobile communication device by the wireless device 500. For example, the application can be downloaded to a memory of each corresponding mobile communication device in response to actions of a corresponding user. The wireless device 500 receives location signals from the mobile communication devices in proximity via the short range wireless transceiver 508. The processor 502 analyzes the location signals from the mobile communication devices to determine that a person associated each corresponding one of the plurality of mobile communication devices is in proximity to the wireless device 500. In various embodiments, the short-range wireless transceiver 508 periodically transmits the beacon signal and receives the location signals and the processor 502 periodically updates the persons in proximity to the wireless device in response thereto.

In one example of operation, the processor 502 executes a classroom attendance application used by an instructor of a class to determine and/or store attendance data indicating attendance in a classroom by students associated with the mobile communication devices. The network 525 can include a local area network, personal area network, the Internet or other public network, a wireless network associated with an educational institution such as a public school, college, university, trade school or other classroom environment, a telecommunications network or other communication network. The processor 502 executes the classroom attendance application to operate in conjunction with the short-range wireless transceiver 508 to communicate RF signals including a beacon signal to identify the wireless device 500 and to facilitate the association of the wireless device 500 with the mobile communication devices in proximity to the wireless device 500. Each of the mobile communication devices includes a mobile communication device processor that executes a student application, downloaded from an app store associated with the operating system of the corresponding mobile communication device, that facilitates location of the corresponding one of the mobile communication devices. The memory 504 stores attendance data indicating that a student associated each corresponding one of the plurality of mobile communication devices is in a classroom associated with the wireless device 500.

In various embodiments, the short-range wireless transceiver 508 periodically transmits the beacon signal and receives the location signals and the attendance data reflects periodic updates to the particular students in the classroom to indicate the students in attendance during a class, students that were tardy, students that leave the classroom during the class and/or students enrolled in the class that are absent.

While in some embodiments, the wireless device 500 can operate to generate and store the attendance data based on location signals received from the mobile communication devices, in other cases, an attendance server can be coupled to network 525 to provide some or all of this functionality. For example, the beacon signal can include an identification signal that identifies the classroom, a class and/or an instructor. In one mode of operation, the mobile communication devices receive the beacon signal and communicate the identification signal to an attendance server 520 via the network 525. The attendance server 520 generates the attendance data and sends the attendance data to the wireless device 500 via the network 525.

Figure 42:
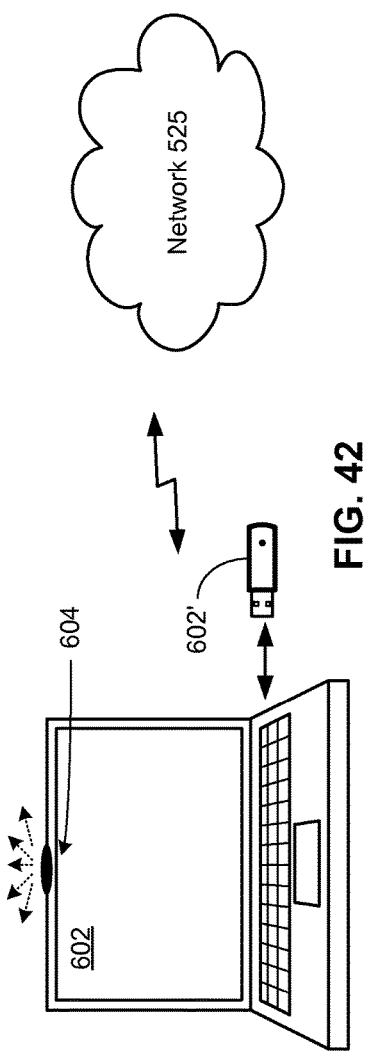
FIG. 42 presents a pictorial representation of wireless device in accordance with an embodiment of the present disclosure.

FIG. 42 presents a pictorial representation of wireless device in accordance with an embodiment of the present disclosure. In particular, a further example of wireless device 500 is presented that operates via personal computer 602 and optionally via USB dongle device 602'. In one mode of operation, the USB dongle device 602' can include the short range wireless transceiver 508 to communicate via network 525. In other examples however, the short range wireless transceiver 508 can be directly incorporated into the personal computer 602.

In a further mode or operation, insertion of the USB dongle device 602' in a USB port of the personal computer 602 causes the processor of the personal computer 602 to launch the classroom attendance application and begin the process of determining attendance. In this example, the classroom attendance application can be stored in a memory of the USB dingle device 602' or stored in a memory of the personal computer 602.

In addition or in the alternative, the personal computer can operate as a classroom attendance device that includes an image capture device 604 such as a still or video camera, infrared camera or imaging device, charge-coupled imaging device or other device configured to capture an image of a classroom and to either trigger the classroom attendance application to update a record indicating the students in the classroom based on location data received via the short range wireless transceiver or to otherwise facilitate the personal computer to identify the students and/or other persons that are present in the classroom. For example, a memory of the personal computer 602 or USB dongle device 602' can store a classroom attendance application that is executed by a processor of the personal computer 602. In operation, the classroom attendance application operates in conjunction with the image capture device 604 to capture a first image of a classroom in conjunction with a class; to analyze the first image of the classroom to identify a plurality of students and other persons in the classroom; and to generate attendance data indicating the plurality of students in the classroom in conjunction with the class.

In various embodiments, the classroom attendance application operates in conjunction with the image capture device 604 to capture a plurality of second images of a classroom in conjunction with the class, to analyze the plurality of second images of the classroom to identify ones of the plurality of students that enter and leave the classroom during the class, and generate the attendance data to indicate the ones of the plurality of students that enter and leave the classroom during the class.

For example, the memory of the personal computer 602 or USB dongle device 602' receives and stores a plurality of image data corresponding to faces of the students enrolled in the class. The student image data can be received from an attendance server that stores student records, can be received by the students when they enroll in the class, can be captured by the students using image capture devices associated with the mobile communication devices and communicated to the personal computer 602 via the network 525 or received from other sources. The classroom attendance application analyzes the first image of the classroom to identify the plurality of students in the classroom using facial recognition to compare faces of the plurality of students in the classroom to the image data corresponding to the faces of the plurality of students enrolled in the class. The classroom attendance application can further analyze the first image of the classroom to identify a person or persons in the classroom that is/are not enrolled in the class.

While described above in terms of attendance, the personal computer 602 can perform other classroom functions as well, such as facilitating a presentation to the class, polling the class for answers to questions, recording quiz results for individual students of the class, providing cumulative scores for the class for presentation to the class, identifying students that are participating in class or not participating in class based on an analysis of image data, providing images that can be used by campus security to identify and respond to public safety risks, class disruptions and other security hazards, and other functions.

Figure 43:
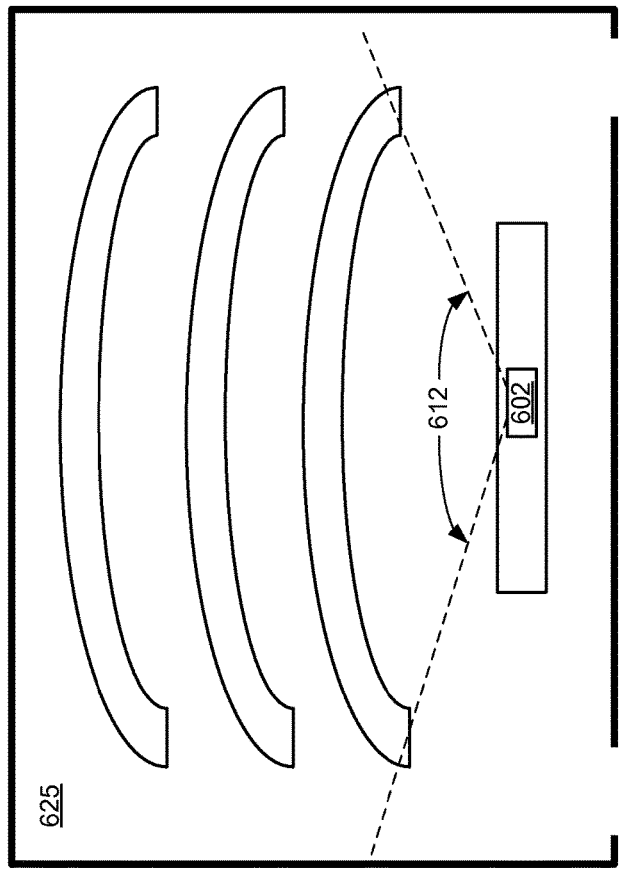
FIG. 43 presents a diagram of classroom in accordance with an embodiment of the present disclosure.

FIG. 43 presents a diagram of classroom in accordance with an embodiment of the present disclosure. In particular, a schematic view of classroom 625 is shown with personal computer capturing image data of the classroom over a field of view 612. In this fashion, an instructor of a class in the classroom 625 can set up the personal computer 602 and launch a classroom attendance application to facilitate an attendance report for the class that indicates students that are present and absent, tardy or who leave class early, and persons that are present but not enrolled in the class, and to perform other classroom functions as well.

FIG. 44 presents a flowchart representation of a method in accordance with an embodiment of the present disclosure. In particular, a method is presented for use with one or more functions and features described in conjunction with FIGS. 1-43. Step 700 includes communicating RF signals including a beacon signal to identify the wireless device and to facilitate the association of the wireless device with the plurality of mobile communication devices in proximity to the wireless device, wherein each corresponding one of the plurality of mobile communication devices includes a mobile communication device processor that executes a student application, downloaded from an app store associated with the operating system of the corresponding one of the plurality of mobile communication devices that facilitates location of the corresponding one of the plurality of mobile communication devices. Step 702 includes storing attendance data indicating that a student associated each corresponding one of the plurality of mobile communication devices is in a classroom associated with the wireless device.

FIG. 45 presents a flowchart representation of a method in accordance with an embodiment of the present disclosure. In particular, a method is presented for use with one or more functions and features described in conjunction with FIGS. 1-44. Step 710 includes capturing a first image of a classroom in conjunction with a class. Step 712 includes analyze the first image of the classroom to identify a plurality of students in the classroom. Step 714 includes generating attendance data indicating the plurality of students in the classroom in conjunction with the class.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A wireless device comprising:
a user interface that generates a pairing signal in response to an indication from a user to associate the wireless device with a plurality of mobile communication devices in proximity to the wireless device;
a short-range wireless transceiver, coupled to the user interface, configured to:
communicate RF signals, in response to the pairing signal from the user, including a beacon signal to identify the wireless device and to facilitate the association of the wireless device with the plurality of mobile communication devices in proximity to the wireless device, wherein each corresponding one of the plurality of mobile communication devices includes a mobile communication device processor that executes an application that facilitates location of the corresponding one of the plurality of mobile communication devices by the wireless device;
receive location signals from the plurality of mobile communication devices in proximity to the wireless device; and
a wireless device processor, coupled to the short-range wireless transceiver and the user interface, that analyzes the location signals from the plurality of mobile communication devices to determine that a person associated each corresponding one of the plurality of mobile communication devices is in proximity to the wireless device.

2. The wireless device of claim 1 wherein the application is downloaded to a memory of the corresponding one of the plurality of mobile communication devices in response to actions of a corresponding user of the corresponding one of the plurality of mobile communication devices.

3. The wireless device of claim 1 wherein the short-range wireless transceiver periodically transmits the beacon signal and receives the location signals and wherein the wireless device processor periodically updates to a plurality of persons in proximity to the wireless device in response thereto.

4. The wireless device of claim 1 wherein the plurality of mobile communication devices include a plurality of mobile phones.

5. The wireless device of claim 1 wherein the short-range wireless transceiver operates in accordance with at least one of: a Bluetooth protocol, a Zigbee protocol or an 802.11 protocol.

6. The wireless device of claim 1 wherein the wireless device processor executes a classroom attendance application, the person associated each corresponding one of the plurality of mobile communication devices is a student and the proximity to the wireless device includes a classroom.

7. The wireless device of claim 1 wherein the plurality of mobile communication devices include at least one first mobile communication device operating via a first operating system and at least one second mobile communication device operating via a second operating system.

8. A wireless device comprising:
a short-range wireless transceiver;
a memory that stores a classroom attendance application;

a wireless device processor, coupled to the short-range wireless transceiver and the memory, that executes the classroom attendance application to:

operate in conjunction with the short-range wireless transceiver to communicate RF signals including a beacon signal to identify the wireless device and to facilitate the association of the wireless device with a plurality of mobile communication devices in proximity to the wireless device, wherein each corresponding one of the plurality of mobile communication devices includes a mobile communication device processor that executes a student application, downloaded from an app store associated with an operating system of the corresponding one of the plurality of mobile communication devices that facilitates location of the corresponding one of the plurality of mobile communication devices; and store attendance data indicating that a student associated each corresponding one of the plurality of mobile communication devices is in a classroom associated with the wireless device.

9. The wireless device of claim 8 wherein the short-range wireless transceiver periodically transmits the beacon signal and the wireless device processor receives location signals and wherein the attendance data reflects periodic updates to a plurality of students in the classroom.

10. The wireless device of claim 8 wherein the plurality of mobile communication devices include a plurality of mobile phones.

11. The wireless device of claim 8 wherein the short-range wireless transceiver operates in accordance with at least one of: a Bluetooth protocol, a Zigbee protocol or an 802.11 protocol.

12. The wireless device of claim 8 wherein the beacon signal includes an identification signal that identifies at least one of: the classroom, a class, or an instructor.

13. The wireless device of claim 12 wherein the plurality of mobile communication devices communicate the identification signal to an attendance server via a network, a wherein the attendance server generates the attendance data and sends the attendance data to the wireless device via the network.

14. The wireless device of claim 13 wherein the network includes the Internet.

15. The wireless device of claim 8 wherein the wireless device includes a personal computer and a universal serial bus (USB) dongle device, and wherein insertion of the USB dongle device in a USB port of the personal computer causes the wireless device processor to launch the classroom attendance application.

16. A classroom attendance device comprising:
an image capture device configured to capture an image of a classroom;
a memory that stores a classroom attendance application;
a processor, coupled to the image capture device and the memory, that executes the classroom attendance application to:
operate in conjunction with the image capture device to capture a first image of a classroom in conjunction with a class;
to analyze the first image of the classroom to identify a plurality of students in the classroom; and
to generate attendance data indicating the plurality of students in the classroom in conjunction with the class.

17. The classroom attendance device of claim 16 wherein the processor executes the classroom attendance application to operate in conjunction with the image capture device to capture a plurality of second images of a classroom in conjunction with the class, to analyze the plurality of second images of the classroom to identify ones of the plurality of students that enter and leave the classroom during the class, and generate the attendance data to indicate the ones of the plurality of students that enter and leave the classroom during the class.

18. The classroom attendance device of claim 16 wherein the memory further stores a plurality of image data corresponding to faces of a plurality of students enrolled in the class and analyzing the first image of the classroom to identify the plurality of students in the classroom includes using facial recognition to compare faces of the plurality of students in the classroom to the image data corresponding to the faces of the plurality of students enrolled in the class.

19. The classroom attendance device of claim 18 wherein the plurality of image data corresponding to the faces of the plurality of students enrolled in the class is received from the plurality of students enrolled in the class.

20. The classroom attendance device of claim 16 wherein the processor executes the classroom attendance application to further:
analyze the first image of the classroom to identify at least one person in the classroom that is not enrolled in the class.

* * * * *